(12) United States Patent
Limem et al.

(10) Patent No.: US 11,904,529 B2
(45) Date of Patent: Feb. 20, 2024

(54) METHODS FOR 3D PRINTING OF POLY-4-HYDROXYBUTYRATE AND COPOLYMERS

(71) Applicant: Tepha, Inc., Lexington, MA (US)

(72) Inventors: Skander Limem, Lynnfield, MA (US); Reshad Bin Harun, Lexington, MA (US); Matthew Dubois, Ayer, MA (US); David P. Martin, Arlington, MA (US); Said Rizk, Windham, NH (US)

(73) Assignee: Tepha, Inc., Lexington, MA (US)

( * ) Notice: Subject to any disclaimer, the term of this patent is extended or adjusted under 35 U.S.C. 154(b) by 0 days.

(21) Appl. No.: 18/187,452

(22) Filed: Mar. 21, 2023

(65) Prior Publication Data

US 2023/0226749 A1 Jul. 20, 2023

Related U.S. Application Data

(62) Division of application No. 17/852,127, filed on Jun. 28, 2022, now Pat. No. 11,639,024, which is a
(Continued)

(51) Int. Cl.
*B33Y 70/00* (2020.01)
*B29C 64/118* (2017.01)
(Continued)

(52) U.S. Cl.
CPC ............ *B29C 64/118* (2017.08); *A61L 27/14* (2013.01); *A61L 29/06* (2013.01); *B29C 64/153* (2017.08);
(Continued)

(58) Field of Classification Search
None
See application file for complete search history.

(56) References Cited

U.S. PATENT DOCUMENTS 11,407,168 B2 8/2022 Limem et al.
11,639,024 B2 5/2023 Limem et al.
(Continued)

FOREIGN PATENT DOCUMENTS

WO WO 2016/019049 A1 2/2016

OTHER PUBLICATIONS

Liang et al., 3D printing of a wearable personalized oral delivery device: A first-in-human study, Sci Adv. May 9, 2018;4(5):eaat2544. doi: 10.1126/sciadv.aat2544. eCollection May 2018 (Year: 2018).*
(Continued)

*Primary Examiner* — Yung-Sheng M Tsui
(74) *Attorney, Agent, or Firm* — Wolf, Greenfield & Sacks, P.C.

(57) ABSTRACT

Methods to fabricate objects by 3D printing of poly-4-hydroxybutyrate (P4HB) and copolymers thereof have been developed. In one method, these objects are produced by continuous fused filament fabrication using an apparatus and conditions that overcome the problems of poor feeding of the filament resulting from the low softening temperature of the filament and heat creep along the fed filament. Methods using an apparatus including a heat sink, a melt tube, a heating block and nozzle, and a transition zone between the heat sink and heating block, with the melt tube extending through the heat sink, transition zone, and heat block to the nozzle are disclosed. 3D objects are also printed by fused pellet deposition (FPD), melt extrusion deposition (MED), selective laser melting (SLM), printing of slurries and solutions using a coagulation bath, and printing using a binding solution and polymer granules.

15 Claims, 13 Drawing Sheets

Related U.S. Application Data division of application No. 16/437,704, filed on Jun. 11, 2019, now Pat. No. 11,407,168.

(60) Provisional application No. 62/683,407, filed on Jun. 11, 2018.

(51) Int. Cl.

| | |
|---|---|
| *B29C 64/321* | (2017.01) |
| *B29C 64/153* | (2017.01) |
| *B29C 64/295* | (2017.01) |
| *B29C 64/209* | (2017.01) |
| *B29C 64/393* | (2017.01) |
| *B29C 64/227* | (2017.01) |
| *B29C 64/268* | (2017.01) |
| *A61L 27/14* | (2006.01) |
| *A61L 29/06* | (2006.01) |
| *B33Y 70/10* | (2020.01) |
| *B33Y 10/00* | (2015.01) |
| *B33Y 30/00* | (2015.01) |
| *B33Y 50/02* | (2015.01) |
| *B29K 67/00* | (2006.01) |

(52) U.S. Cl.
CPC .......... *B29C 64/209* (2017.08); *B29C 64/227* (2017.08); *B29C 64/268* (2017.08); *B29C 64/295* (2017.08); *B29C 64/321* (2017.08); *B29C 64/393* (2017.08); *B33Y 70/00* (2014.12); *B33Y 70/10* (2020.01); *B29K 2067/04* (2013.01); *B33Y 10/00* (2014.12); *B33Y 30/00* (2014.12); *B33Y 50/02* (2014.12)

(56) References Cited

U.S. PATENT DOCUMENTS

| | | | |
|---|---|---|---|
| 2018/0049858 A1* | 2/2018 | Tao | A61L 31/06 |
| 2019/0375149 A1 | 12/2019 | Limem et al. | |
| 2019/0375153 A1* | 12/2019 | Achten | C08G 18/4238 |
| 2020/0405473 A1* | 12/2020 | Nanni | A61L 27/3625 |
| 2021/0017319 A1* | 1/2021 | Hong | B33Y 10/00 |
| 2021/0070987 A1* | 3/2021 | Taylor | C08L 71/02 |
| 2022/0324162 A1 | 10/2022 | Limem et al. | |

OTHER PUBLICATIONS

Liang et al., 3D printing of a wearable personalized oral delivery device: A first-in-human study. Sci Adv. May 9, 2018;4(5):eaat2544(1-11). doi: 10.1126/sciadv.aat2544.

* cited by examiner

METHODS FOR 3D PRINTING OF POLY-4-HYDROXYBUTYRATE AND COPOLYMERS

CROSS-REFERENCE TO RELATED APPLICATIONS

This Application is a Divisional of U.S. application Ser. No. 17/852,127, filed Jun. 28, 2022, which is a Divisional of U.S. application Ser. No. 16/437,704, filed Jun. 11, 2019, which claims the benefit of U.S. Provisional Application No. 62/683,407, filed Jun. 11, 2018, each of which is hereby incorporated herein by reference in its entirety.

FIELD OF THE INVENTION

The present invention generally relates to methods for fabricating objects by 3D printing of poly-4-hydroxybutyrate (P4HB), copolymers and blends thereof, equipment and conditions that allow continuous printing of these objects, and the use of these methods to produce medical implants for uses that include plastic and reconstructive surgery including mastopexy and breast reconstruction, general surgery including hernia repairs and anti-adhesion devices, tissue engineering, drug delivery, pelvic floor reconstruction, treatment of stress urinary incontinence, nerve repair, periodontal surgery, oral surgery, orthopedic surgery, stenting, vascular and cardiovascular surgery.

BACKGROUND OF THE INVENTION

3D Printing is a computer controlled process whereby a three-dimensional object can be fabricated from a 3D CAM (Computer Aided Design) model using an additive manufacturing approach. Objects may be fabricated by depositing, joining, or solidifying material, typically a metal or plastic material.

In fused filament fabrication (FFF), a plastic, preferably a thermoplastic, in the form of a filament, is fed into a heating block to melt the plastic, and thin threads are extruded through a movable nozzle onto the surface of a stage in a predetermined pattern to form a 3D object. The threads typically have a thickness of 50 µm to 1 mm, and adhere to one another with the underlying layer hardening as the plastic cools and binding to the new layer that is added on top. Layers of the extruded plastic are built up to form the three-dimensional object as the nozzle is moved by a computer. In a variation of the technique, the object may be formed on a movable stage controlled by a computer with the nozzle remaining in the same position, or in a further variant, the object may be formed with both the positions of the nozzle and the stage controlled by a computer.

A standard equipment set up for FFF of a thermoplastic polymer, comprises a feeder mechanism for the filament. The feeder mechanism grips the filament and feeds it at a controlled rate into an extruder comprising a heater block and nozzle. A stage is positioned under the nozzle, and the object is printed on the stage either by moving the nozzle, the stage or both, under the control of a computer, in three dimensions. The part of the equipment that is responsible for feeding the filament is often referred to as the cold end. This typically comprises gears and rollers that grip the filament, and feed it with torque provided by a drive motor into the extruder. The feeder mechanism controls the rate at which the filament is delivered to the extruder. The heater block and the nozzle are called the hot end. In the hot end, the filament is melted and exits the nozzle forming a thin thread that is deposited on the stage to form the 3D printed object. The speed of the process is controlled so that there is sufficient time for the polymer under the nozzle to have solidified before additional extrudate from the nozzle is applied on top of it.

There is a need for a method and new equipment to process polymers by 3D printing using FFF, such as P4HB and copolymers thereof, that are not printable at a temperature just above their melt temperature, but instead require significantly elevated temperatures in order for the polymer's melt viscosity to be low enough to allow printing. At the same time, the process must ensure that the temperature in the cold end does not exceed the softening temperature of the polymer, and is preferably lower than the softening temperature. The process also needs to be designed to ensure that polymers that do not rapidly solidify at elevated temperatures, such as P4HB and copolymers thereof, solidify after printing in order to produce products with good print quality.

U.S. Pat. No. 5,121,329 to Crump discloses equipment suitable for FFF of material that (i) can be melted at a temperature slightly above its melting temperature, preferably just one degree above its melting temperature, and (ii) has a solidification temperature that permits the material to solidify substantially instantaneously at room temperature. Crump does not disclose equipment suitable for FFF of a thermoplastic, such as P4HB, that must be heated to more than twice its melt temperature in order for the polymer to flow, that has a low softening temperature, and that solidifies slowly from the melt.

WO2016/019049 to Church et al. discloses equipment for FFF that includes a heat sink and fan to dissipate heat. Church also does not disclose equipment suitable for FFF of a thermoplastic like P4HB that must be heated to at least twice its melt temperature in order for the polymer to flow, that has a low softening temperature, and that solidifies slowly from the melt. Church et al. do not disclose equipment for FFF comprising a shroud fixed to the print head, a heat shield, an insulator to prevent contact of the heat shield and hot end, and a cooled flat print stage.

There is also a need for methods to process P4HB and copolymers thereof by 3D printing using fused pellet deposition (FPD), melt extrusion deposition (MED), selective laser melting (SLM), printing of slurries and solutions using a coagulation bath, and printing using a binding solution and granules of powder.

Chiulan et al. Recent advances in 3D printing of aliphatic polyesters, *Bioengineering* 2018, 5, 2; doi:10.3390/bioenginnering5010002 discloses fused deposition modeling of poly-3-hydroxybutyrate (P3HB), and poly-3-hydroxybutyrate-co-3-hydroxyvalerate (PHBV) with maleic anhydride and palm fibers, wood flower, and carbon nanotubes in order to enhance the properties of the fibers. It should be noted, however, that poly-4-hydroxybutyrate (P4HB) has entirely different properties compared to P3HB ("PHB") despite their similar names. For example, P3HB has a melting point of 180° C. versus a melting point of about 60° C. for P4HB. The polymers also have substantially different glass transition temperatures and mechanical properties. P4HB has a glass transition temperature of −55° C. whereas P3HB has a glass transition temperature of 0° C. PHB is a relatively hard brittle polymer with an extension to break of just a few percent, whereas P4HB is a strong extensible polymer with an extension to break of about 1000%. P4HB has strikingly different uses from P3HB, as well as significantly different processing requirements. For example, P3HB can be melt processed at just a few degrees above its melt temperature, whereas P4HB needs to be melt processed typically at temperatures over 150° C. due to its high melt viscosity despite having a melting point of only 60° C.

Derakhshanfar et al. 3D bioprinting for biomedical devices and tissue engineering: a review of recent trends and advances, *Bioactive Materials*, 3:144-156 (2018) reviews 3D printing methods and discloses that "not all biomaterials are printable and those which are printable may not be printable in a wide range of processing parameters."

Thus, there is currently no disclosure of how P4HB and copolymers thereof can be processed by 3D printing including the equipment and conditions necessary for continuous printing of high quality objects. There is also no disclosure of how to prevent significant drops in the molecular weight of P4HB and copolymers thereof during printing.

It is therefore an object of the present invention to provide new 3D printers suitable for 3D printing of P4HB and copolymers thereof.

It is another object of the present invention to provide multiple means of 3D printing P4HB and copolymers thereof.

It is a further object of the present invention to provide objects of P4HB and copolymers thereof produced by 3D printing characterized by specific physical properties.

It is still another object of the present invention to provide objects of P4HB and copolymers thereof with controlled degradation profiles that can be used in medical applications as implants.

SUMMARY OF THE INVENTION

Methods to fabricate objects by 3D printing of poly-4-hydroxybutyrate and copolymers thereof have been developed. In one method, the objects are produced by continuous fused filament fabrication using new 3D printers and improved processing conditions that allow the temperature of the hot end to be 3-5× higher than the melt temperature of the polymer, yet maintain the cold end at a temperature well below the softening temperature of the polymer. The equipment setup, processing conditions, and polymer feed specifications allow the process to run continuously without interruptions in feeding, without the formation of polymer plugs resulting from the high temperatures required in the hot end, and without significant reductions in the polymer's molecular weight. Furthermore, the methods also improve the print quality of the object by maintaining a uniform temperature across the printing stage, and providing conditions that allow rapid solidification of the polymer to form the object. The new methods make it possible for objects of P4HB and copolymers thereof to be printed with print lines, wherein the dimensions of the print lines are within 10% of the expected dimensions of the print lines. A preferred embodiment includes a 3D printed object of poly-4-hydroxybutyrate or copolymer thereof, wherein the object is printed by FFF with the hot end at a temperature of 150-300° C., the temperature of the cold end is −50° C. to 42° C., more preferably 0° C. to 35° C., and the diameter of the filament feed is not greater than 94% of the diameter of the melt tube at the point of entry into the hot end.

Other methods for 3D printing of P4HB and copolymers thereof have also been developed. These methods include fused pellet deposition (FPD), melt extrusion deposition (MED), selective laser melting (SLM), printing of slurries and solutions using a coagulation bath, and printing using a binding solution and granules of powder.

In some particularly preferred embodiments, the disclosed compositions and methods do not include a foaming/blowing agent.

DETAILED DESCRIPTION OF THE INVENTION

Figure 1:
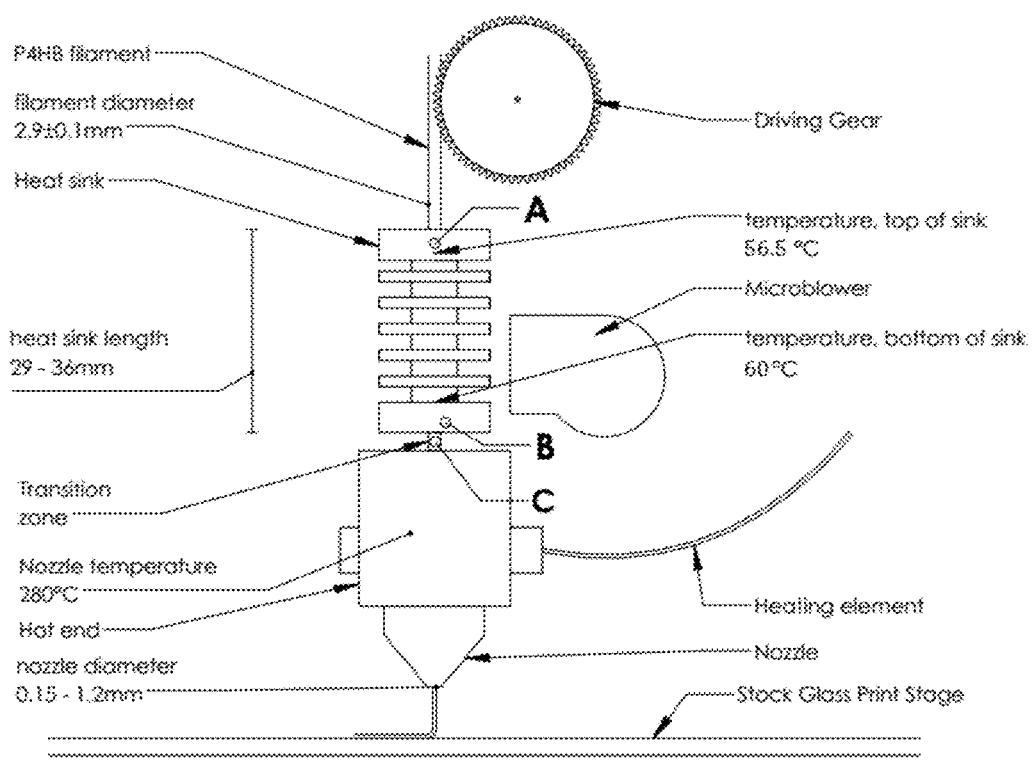
FIG. 1 is a diagram showing a typical equipment set up for FFF. The diagram shows the location of position A where the temperature at the top of the heat sink is measured, the location of position B where the temperature at the bottom of the heat sink is measured, and the location of position C where the temperature in the transition zone is measured.

It would be desirable to identify conditions and equipment that are suitable for preparing objects comprising poly-4-hydroxybutyrate or copolymers thereof by 3D printing. It would be particularly desirable to identify methods to 3D print objects from P4HB and copolymers thereof that provide good quality objects, and processes that can run continuously without interruption of the print job.

In one preferred embodiment, it would be desirable to identify a FFF process that allows continuous production of objects comprising P4HB and copolymers thereof, and overcomes the following issues that are encountered when using standard FFF equipment to print these polymers: (i) inconsistent feeding of the filament into the hot end due to loss of traction of the feeder mechanism on the filament; (ii) plugging of the polymer prior to entry into the hot end; (iii) significant reduction in polymer molecular weight due to slow print speeds; (iv) poor print quality due to slow solidification of the polymer; and (v) jamming of the filament feed or slippage of the filament feed due to lack of uniformity of the diameter of the filament, or under/oversizing the diameter of the filament.

The new equipment and methods described herein make it possible to continuously print P4HB and copolymers thereof, and provide significant improvements in print quality, structural integrity (which is a function of the continuity of the printed line, layer to layer adhesion, and optionally adhesion of the first layer to the stage), and print speed. In one embodiment, the new methods utilize new equipment that makes it possible to print polymers such as P4HB and copolymers thereof that: (i) are extremely viscous in the melt and require very high processing temperatures, and (ii) solidify very slowly from the melt. In one preferred embodiment, continuous printing by FFF of P4HB and copolymers thereof is made possible by improvements that: (a) significantly reduce the temperature of the filament as it is fed into the hot end without decreasing the melt processing temperature, (b) reduce the temperature of the polymer prior to entry into the hot end without decreasing the melt processing temperature, (c) reduce the loss of molecular weight of the polymer during printing, (d) facilitate more rapid solidification of the polymer after printing by cooling of the extrudate, (e) produce filaments for printing with highly uniform diameters, and (f) define specific ratios of the diameters of the filament versus the diameters of the melt tube.

In order to continuously print P4HB and copolymers thereof, FFF equipment has been improved with a number of new features that include a system to significantly cool the temperature of the filament at the top of the heat sink and before it enters the hot end, and a method to cool the printed polymer exiting the nozzle in the hot end. In one embodiment, the cooling system of the improved FFF equipment comprises a shroud surrounding the heat sink incorporating an air nozzle directed at the lowest fin of the heat sink and an insulator and heat shield located between the heat sink and the hot end. The heat shield prevents high pressure air hitting the hot end which can result in heating failures, and thermal errors of printer hardware including interruption and termination of printing. The insulator prevents the heat shield being exposed to the high temperature in the hot end required to print P4HB and copolymers thereof which would otherwise deform the heat shield. In order to improve the print quality, the new FFF 3D printer may further incorporate a novel print stage designed to increase the solidification rate of the hot extrudate of P4HB or copolymers thereof, and also to improve the print quality of the first print layer. In a further embodiment, the new FFF 3D printer incorporates a print stage made from aluminum that can be cooled. The use of an aluminum stage results in a significantly improved first print layer and layer adhesion of P4HB or copolymer thereof due to the evenness of the aluminum surface compared to current commercial stages typically made from ethylene imine based (PEI) films or glass. Furthermore, cooling of the aluminum stage facilitates more rapid solidification of the polymer which is otherwise slow to solidify, and allows the underlying layer of polymer to harden before a new layer of polymer is printed on top. The more rapid solidification resulting from cooling of the stage results in significantly improved print quality.

In addition to the development of new equipment and methods to 3D print P4HB and copolymers thereof by FFF, methods have also been developed to 3D print P4HB and copolymers by fused pellet deposition (FPD), melt extrusion deposition (MED), selective laser melting (SLM), printing of slurries and solutions using a coagulation bath, and printing using a binding solution and granules of powder.

In a preferred embodiment, the new 3D printers and methods disclosed herein may be used to produce 3D printed objects comprising P4HB and copolymers thereof. In a particularly preferred embodiment, the new 3D printers and methods disclosed herein may be used to produce 3D printed objects comprising P4HB and copolymers thereof that may be used to produce medical implants for uses that include plastic and reconstructive surgery including mastopexy and breast reconstruction, general surgery including hernia repairs and anti-adhesion devices, tissue engineering, drug delivery, pelvic floor reconstruction, treatment of stress urinary incontinence, nerve repair, periodontal surgery, oral surgery, orthopedic surgery, stenting, vascular and cardiovascular surgery. The new 3D printers make it possible to produce three-dimensional medical devices comprising P4HB and copolymers thereof that cannot be produced by other fabrication methods. Optionally, the devices may further comprise bioactive agents, including antibiotics, and other additives. In particularly preferred embodiment, the method of making 3D objects and the resulting 3D printed objects do not include a blowing/foaming agent. For example, a blowing/foaming agent may be a substance having a gas volume of 100 to 350 mL/g, which decomposes at a temperature higher than the decomposition temperature thereof, for example, at a printer nozzle temperature to release gas. Examples of the foaming agent include azodicarbonamide, modified azodicarbonamide, p-toluenesulfonyl semicarbazide, p-toluenesulfonyl hydrazide, but are not limited to, hydrazide, p-toluenesulforyl acetone hydrazide, 5-phenvitetrazole, sodium bicarbonate, or combinations thereof. For example, the foaming agent may be a substance that decomposes at 130 to 250° C. to generate gas.

I. Definitions

"3D Printing" as generally used herein means a computer controlled process whereby a three-dimensional object can be fabricated from a 3D CAM model using additive manufacturing.

"Additive manufacturing" as generally used herein means a process by which an object is formed by depositing layer upon layer of material.

"Bioactive agent" is used herein to refer to therapeutic, prophylactic or diagnostic agents, such as agents that promote healing and the regeneration of host tissue and therapeutic agents that prevent, inhibit or eliminate a disease or disorder.

"Bioceramic" means a ceramic suitable for use or replacement in the human body.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer formed of two or more different monomers.

"Ceramic" means an inorganic, nonmetallic solid prepared by the action of heat and subsequent cooling.

"Cold end" as generally used herein means the part of the equipment for FFF that is responsible for feeding the filament into the extruder.

"Copolymers of poly-4-hydroxybutyrate" as generally used herein means any polymer including 4-hydroxybutyrate with one or more different hydroxy acid units.

"DOD" as used herein means drop-on-demand printing.

"Feed rate" as generally used herein in FFF means the speed at which the filament is fed or loaded into the heat sink.

"FFF" as used herein means fused filament fabrication.

"FPD" as used herein means fused pellet deposition.

"Heat sink" as generally used herein refers to a heat exchanger that transfers and dissipates heat generated by the hot end in FFF.

"Hot end" as generally used herein means the part of the equipment for FFF that is responsible for heating the filament, namely the heater block and nozzle.

"Implant" as generally used herein include medical devices that are used in vivo as well as those that contact the surface of the body or are inserted into any orifice of the body.

"MED" as used herein means melt extrusion deposition.

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer including 4-hydroxybutyrate units. It may be referred to herein as P4HB or TephaFLEX® biomaterial (manufactured by Tepha, Inc., Lexington, MA).

"Print quality" as generally used herein refers to the resolution of the print in the X, Y and Z directions of a Cartesian coordinate system (wherein the Z direction is the height of a printed layer). An object printed with good print quality has print dimensions that are within 10% of the expected value. For example, an object printed with a resolution of 100 microns in the X and Y directions, and 50 microns in the Z direction has good print quality if the line width in the X and Y directions is between 90 and 110 microns, and between 45 and 55 microns in the Z direction.

"Print speed" as generally used herein in FFF means the linear speed of the moving print stage, the linear speed of the moving nozzle, or the linear speed that results from the combination of the linear speed of the print stage and linear speed of the moving nozzle.

"Residence time" as generally used herein refers to the average time in seconds that a one cubic millimeter volume of molten polymer spends in the hot end in FFF, and is typically expressed as $s/mm^3$, or the average time that the polymer spends in the horizontal extruder in MED and is typically expressed as $s/cm^3$ or $min/cm^3$.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body, whether degradation is due mainly to hydrolysis or mediated by metabolic processes.

"SLM" as used herein means selective laser melting.

II. Compositions

Methods and improved 3D printers have been developed to prepare three-dimensional objects comprising P4HB and copolymers thereof. The objects can be used in vivo for soft or hard tissue repair, regeneration and remodeling applications. In a preferred embodiment, the objects are medical devices or may be converted into medical devices through further processing.

A. P4HB Homopolymer & Copolymer

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, MA). Poly-4-hydroxybutyrate (P4HB, TephaFLEX® biomaterial) is a strong, pliable absorbable thermoplastic polyester.

The P4HB polymer belongs to a larger class of materials called polyhydroxyalkanoates (PHAs) that are produced by numerous microorganisms (see, for example, Steinbüchel A., et al. Diversity of Bacterial Polyhydroxyalkanoic Acids, *FEMS Microbial. Lett.* 128:219-228 (1995)). In nature, these polyesters are produced as storage granules inside cells, and serve to regulate energy metabolism. They are also of commercial interest because of their thermoplastic properties, biodegradability and relative ease of production.

Chemical synthesis of P4HB has been attempted, but it has been impossible to produce the polymer with a sufficiently high molecular weight that is necessary for most applications, including melt processing (see Hori, Y., et al., *Polymer* 36:4703-4705 (1995); Houk, K. N., et al., *J. Org. Chem.*, 2008, 73 (7), 2674-2678; and Moore, T., et al., *Biomaterials* 26:3771-3782 (2005)). In fact, it has been calculated to be thermodynamically impossible to chemically synthesize a high molecular weight homopolymer under normal conditions (Moore, T., et al., *Biomaterials* 26:3771-3782 (2005)). Chemical synthesis of P4HB instead yields short chain oily oligomers that lack the desirable thermoplastic properties of the high molecular weight P4HB polymers produced by biosynthetic methods.

U.S. Pat. Nos. 6,245,537, 6,623,748, 7,244,442, 8,231,889, 9,290,612, and 9,480,780 describe methods of making PHAs with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and 9,162,010 describe use of PHAs to make medical devices. Copolymers of P4HB include 4-hydroxybutyrate copolymerized with 3-hydroxybutyrate or glycolic acid (U.S. Pat. No. 8,039,237 to Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III,* 4:91-127 (2002), and by Martin, D. et al. Medical Applications of Poly-4-hydroxybutyrate: A Strong Flexible Absorbable Biomaterial, *Biochem. Eng. J.* 16:97-105 (2003). Medical devices and applications of P4HB have also been disclosed by U.S. Pat. No. 6,548,569 to Williams et al. Several patents including U.S. Pat. Nos. 6,555,123, 6,585,994, 7,025,980, 9,532,867, and 9,277,986 describe the use of PHAs in tissue repair and engineering. U.S. Pat. Nos. 8,034,270, 8,016,883, 8,287,909, 8,747,468, 9,511,169, 9,457,127 and 9,555,155 disclose fibers, nonwovens, and textiles made by melt extrusion of P4HB.

Sodian et al. Application of stereolithography for scaffold fabrication for tissue engineered heart valves, ASAIO Journal 48:12-16 (2002) discloses the fabrication of molds to make tissue engineered heart valves comprising P4HB using 3D printing, but does not disclose 3D printing of P4HB and copolymers thereof or 3D printed objects comprising P4HB and copolymers thereof.

The processes described herein are used with poly-4-hydroxybutyrate (P4HB) and copolymers thereof. P4HB homopolymer can be obtained from Tepha, Inc. of Lexington, MA, USA. The P4HB homopolymer can have a weight average molecular weight, Mw, within the range of 50 kDa to 1,200 kDa (by GPC relative to polystyrene) and more preferably from 100 kDa to 1,000 kDa and even more preferably from 100 kDa to 500 kDa. The polymer may include the P4HB homopolymer or copolymer blended with other absorbable polymers, additives, or bioactive agents, including cells.

B. Blends of P4HB & Copolymers Thereof

Objects comprising blends of P4HB or copolymers thereof may be printed using the methods and equipment disclosed herein. In one embodiment, P4HB and copolymers thereof can be blended with other absorbable polymers, including, but not limited to: poly(lactides); poly(glycolides); poly(lactide-co-glycolides); poly(lactic acid); poly(glycolic acid); poly(lactic acid-co-glycolic acid); poly-caprolactones; poly(orthoesters); polyanhydrides; poly(phosphazenes); polyhydroxyalkanoates (including P3HB and poly-3-hydroxybutyrate-co-3-hydroxyvalerate, PHBV); synthetically or biologically prepared polyesters (including polyesters with one or more of the following monomeric units: glycolic, lactic; trimethylene carbonate, p-dioxanone, or C-caprolactone); poly(lactide-co-caprolactones); polycarbonates; tyrosine polycarbonates; polyamides (including synthetic and natural polyamides, polypeptides, and poly(amino acids)); polyesteramides; poly(dioxanones); poly(alkylene alkylates); polyethers (such as polyethylene glycol, PEG, and polypropylene oxide, PPO) or other hydrophilic or water soluble polymers such as polyvinyl pyrrolidones (PVP); polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; biocompatible polysaccharides; biocompatible copolymers (including block copolymers or random copolymers); with blocks of other biocompatible or biodegradable polymers, for example, poly(lactide), poly(lactide-co-glycolide, or polycaprolactone or combinations thereof. Other polymers and materials that can be printed with P4HB and copolymers thereof include alginate, silk, glycerol, gelatin, hyaluronic acid and derivatives thereof, collagen, polyvinyl alcohol, and hydrogels.

C. Incorporation of Additives into Compositions of P4HB and Copolymers Thereof

Certain additives may be incorporated into the compositions comprising P4HB and copolymers thereof prior to 3D printing of the compositions. In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts of up to 20% by weight. Nucleating agents may be incorporated to increase the rate of crystallization of the compositions comprising P4HB and copolymers thereof. Such agents may be used to improve the printing of the objects and the mechanical properties of the objects. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine. Plasticizers that may be incorporated include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

In another embodiment, the additives are contrast agents, radiopaque markers or radioactive substances.

In yet another embodiment, the additives are ceramics, more preferably bioceramics, and even more preferably resorbable bioceramics. Examples of resorbable bioceramics that can be incorporated into the compositions of P4HB and copolymers thereof prior to printing include tricalcium phosphate (α and β forms of tricalcium phosphate (TCP)—with a nominal composition of $Ca_3(PO_4)_2$), biphasic calcium phosphate (BCP), hydroxylapatite, calcium sulfate, calcium carbonate, and other calcium phosphate salt-based bioceramics. Bio-active glasses may also be incorporated. Bioactive glasses include bioactive glasses composed of $SiO_2$, $Na_2O$, $CaO$ and $P_2O_5$ in specific proportions. In an embodiment, the P4HB blends comprise resorbable bioceramics with a size distribution ranging from nanoparticles to microparticles. In a preferred embodiment, the ceramics have particle sizes of less than 100 microns. In a still further embodiment, the additives may be cross-linking agents.

In some particularly preferred embodiments, the disclosed compositions and methods do not include a foaming/blowing agent. For example, a blowing/foaming agent may be a substance having a gas volume of 100 to 350 mL/g, which decomposes at a temperature higher than the decomposition temperature thereof, for example, at a printer nozzle temperature to release gas. Examples of the foaming agent include azodicarbonamide, modified azodicarbonamide, p-toluenesulfonyl semicarbazicle, p-toluenesuifonyl hydrazide, but are not limited to, hydrazide, p-toluenesulfonyl acetone hydrazide, 5-phenvitetrazole, sodium bicarbonate, or combinations thereof. For example, the foaming agent may be a substance that decomposes at 130 to 250° C. to generate gas.

D. Incorporation of Bioactive Agents and Cells into Compositions of P4HB and Copolymers Thereof If desired, the compositions of P4HB and copolymers thereof may incorporate bioactive agents. These agents may be added prior to printing of the compositions into objects or after the objects have been formed.

In one embodiment, the bioactive agents and the composition comprising P4HB or copolymer thereof, may be dissolved in a solvent or solvent system in order to disperse the bioactive agent in the polymer, and the solvent may then be removed by evaporation. Preferred solvents include methylene chloride, chloroform, tetrahydrofuran, acetone, dimethylformamide, and 1,4-dioxane.

Examples of bioactive agents that can be incorporated into the compositions of P4HB and copolymers thereof, include, but are not limited to, physiologically or pharmacologically active substances that act locally or systemically in the body. Bioactive agents include biologically, physiologically, or pharmacologically active substances that act locally or systemically in the human or animal body. Examples can include, but are not limited to, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, peptides, proteins, glycoproteins, anesthetics, hormones, antibodies, growth factors, fibronectin, laminin, vitronectin, integrins, antimicrobials, steroids, hydroxyapatite, silver particles, vitamins, non-steroidal anti-inflammatory drugs, chitosan and derivatives thereof, alginate and derivatives thereof, collagen, sugars, polysaccharides, nucleotides, oligonucleotides, lipids, lipoproteins, hyaluronic acid and derivatives thereof, allograft material, xenograft material, ceramics, nucleic acid molecules, antisense molecules, aptamers, siRNA, nucleic acids, and combinations thereof.

Antimicrobial agents that may be incorporated into the compositions of P4HB and copolymers thereof, or coated on those compositions, include, but are not limited to, antibacterial drugs, antiviral agents, antifungal agents, and antiparisitic drugs. Antimicrobial agents include substances that kill or inhibit the growth of microbes such as microbicidal and microbiostatic agents.

Antimicrobial agents that may be incorporated into the compositions of P4HB and copolymers thereof, include, but are not limited to: rifampin; minocycline and its hydrochloride, sulfate, or phosphate salt; triclosan; chlorhexidine; vancomycin and its hydrochloride, sulfate, or phosphate salt; tetracycline and its hydrochloride, sulfate, or phosphate salt, and derivatives; gentamycin;

cephalosporin antimicrobials; aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts, ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; clarithromycin; and silver ions, salts, and complexes. In a preferred embodiment, the antimicrobial agents incorporated into the compositions of P4HB and copolymers thereof or coated on those compositions are (i) rifampin and (ii) minocycline and its hydrochloride, sulfate, or phosphate salt.

If desired, the compositions of P4HB and copolymers thereof may incorporate cells, including, cells of epithelial, connective, muscular and nervous tissues. Such compositions may be printed to form bioprinted objects, including tissue engineering scaffolds. The latter may be used, for example, in the repair, regeneration or replacement of tissue structures and organs, including skeletal defects and bone regeneration.

III. Methods and Equipment for 3D Printing of Compositions Comprising P4HB and Copolymers Thereof A. Equipment for FFF of P4HB and Copolymers Thereof FIG. 1 is a diagram showing a typical equipment set up for 3D printing by FFF. The equipment comprises a feeder mechanism for the filament, a heat sink that is cooled by a microblower directing air all along the heat sink, a transition zone between the heat sink and hot end, a hot end comprising a heater block and nozzle, and a stock glass printing stage. This equipment is suitable for 3D printing a wide variety of polymers such as polyethylene terephthalate (PET), polylactic acid (PLA), polystyrene (PS), nylon, and acrylonitrile butadiene styrene (ABS). Attempts to print P4HB using this equipment setup, failed, however, because of differences in properties between P4HB and the properties of the polymers that the equipment in FIG. 1 was designed to process. When 3D printing of P4HB was attempted with this equipment, the high temperature required in the hot end was conducted to the cold end with dire consequences. As shown in Table 1, when the P4HB polymer was heated in the hot end to 280° C., the temperature measured at the bottom of the heat sink rose to 60° C. and the temperature at the top of the heat sink increased to 56.5° C. Since P4HB has a melting temperature of about 60° C. and becomes soft in the range of 42 to 58° C., the temperatures in the heat sink were above the range at which P4HB softens, and very close to the melting temperature of P4HB at the bottom of the heat sink. These high temperatures in the heat sink resulted in the formation of a soft plug of P4HB at the bottom of the heat sink, and loss of traction on the filament at the top of the heat sink causing print failure.

A number of further attempts were made to print P4HB using the equipment shown in FIG. 1 by lowering the temperature in the hot end. The temperatures measured at the top of the heat sink (position A), the bottom of the heat sink (position B), and at the transition zone (position C) when the temperature in the hot end was decreased are also shown in Table 1. Decreasing the temperature in the hot end did result in some decrease in the temperatures at the top and the bottom of the heat sink, however, problems continued to be encountered because the temperatures in the heat sink were still too close to the softening temperature of P4HB. As is evident from Table 1, when temperatures in the hot end were 180-280° C., the temperatures at the top of the heat sink ranged from 45° C. to 56.5° C. due to heat creep from the hot end. Even at the lowest temperature (180° C. in the hot end) where the melt viscosity of P4HB was still fairly high and print quality was not optimal, slippage of the driving gears in the feeder mechanism continued to occur, due to softening of the P4HB filament, resulting in inconsistent feeding, poor print quality, and eventually interruption of printing. The microblower was incapable of providing sufficient cooling to produce a thermal profile along the heat sink necessary for continuous printing of P4HB and copolymers thereof.

TABLE 1

Relationship between temperatures in hot and cold ends during attempted processing of P4HB using standard FFF equipment shown in FIG. 1

| | Zone/Nozzle Temp. (° C.) | | | | | |
|---|---|---|---|---|---|---|
| | 180 | 200 | 220 | 240 | 260 | 280 |
| Top of heat sink, A | 45 | 46 | 48 | 49 | 53 | 56.5 |
| Bottom of heat sink, B | 47 | 48 | 48 | 52 | 57 | 60 |
| Transition zone, C | 65 | 89 | 100 | 104 | 118 | 127 |

Figure 2:
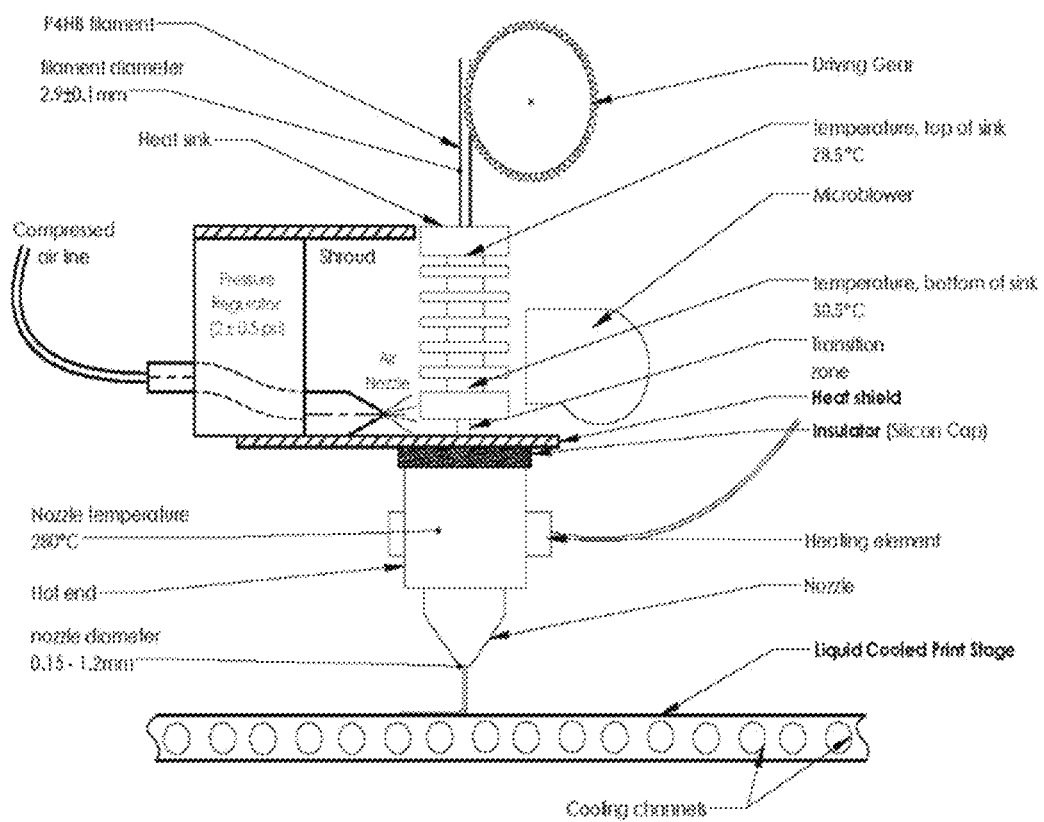
FIG. 2 is a diagram showing a new 3D printer designed for FFF of poly-4-hydroxybutyrate or copolymer thereof comprising an air nozzle within a shroud directed at the lower fin of the heat sink, an insulator (silicon cap) between the heat sink and the hot end, and a cooled print stage. The diagram shows the temperatures measured at the bottom of the heat sink (30.5° C.) and the top of the heat sink (28.5° C.) when the hot end is at a temperature of 280° C.

A number of improvements were made to the standard equipment set up for FFF shown in FIG. 1 in order to prevent the P4HB filament from slipping in the feeder mechanism, and to prevent the formation of soft plugs at the bottom of the heat sink. The improvements are shown in FIG. 2, and include (i) the incorporation of a shroud around the heat sink with a compressed air line that focuses a stream of cooling air on the bottom fin of the heat sink, (ii) the incorporation of a heat shield in the transition zone between the hot end and the heat sink to prevent cooling air from impacting the hot end and damaging the printed structure on the stage, (iii) the incorporation of an insulator between the hot end and the heat shield to prevent distortion of the heat shield by the heat from the hot end, and (iv) replacement of the printing stage with a stage that has a flatter surface, and can be cooled. These improvements make it possible to fabricate objects of P4HB and copolymers thereof by FFF using the conditions described herein.

As a result of the improvements described above and shown in FIG. 2, it was possible to lower the temperature of the heat sink during FFF of P4HB and copolymers thereof, and obtain objects with good print quality. Table 2 shows the improved temperature profile of the heat sink and transition zone that resulted from the improvements when P4HB filament was processed by FFF using the equipment set up shown in FIG. 2. At the highest temperature in the hot end of 280° C., the temperatures at the top and bottom of the heat sink were lowered from 56.5° C. and 60° C., respectively (see Table 1), to 28.5° C. and 30.5° C., respectively, when compressed air at a pressure of 2±0.5 psi (13.8±3.5 kPa) was directed at the heat sink (see Table 2). Notably, the temperatures at the heat sink (28.5-30.5° C.) using the new equipment set up shown in FIG. 2 were well below the softening temperature range of 42-58° C. for P4HB. As the temperature in the hot end was decreased from 280° C., there was a progressive further decrease in the temperatures in the heat sink. At a temperature of 220° C. in the hot end, the temperatures at the top and bottom of the heat sink were 27 and 29° C., respectively, which further decreased at a hot end temperature of 180° C. to 26.5 and 27.5° C., respectively, as shown in Table 2. Table 2 also shows the progressive decrease in the temperature of the transition zone resulting from the equipment set up shown in FIG. 2. With the equipment set up shown in FIG. 1, the temperature in the transition zone when the hot end was at 280° C. was 127° C. (see Table 1). Using the improved equipment set up shown in FIG. 2, this temperature decreased to 91° C., when the temperature in the hot end was also at 280° C. (see Table 2). At lower temperatures in the hot end, the temperatures in the transition zone decreased further as shown in Table 2.

TABLE 2

Relationship between temperatures in hot and cold ends during processing of P4HB using modified FFF equipment shown in FIG. 2

| | Zone/Nozzle Temp. (° C.) | | | | | |
|---|---|---|---|---|---|---|
| | 180 | 200 | 220 | 240 | 260 | 280 |
| Top of heat sink, A | 26.5 | 27 | 27 | 27.5 | 28 | 28.5 |
| Bottom of heat sink, B | 27.5 | 28 | 29 | 29 | 29.5 | 30.5 |
| Transition zone, C | 65 | 70 | 75 | 81 | 86.5 | 91 |

In a preferred embodiment, the temperature of the filament during FFF of P4HB and copolymers thereof at the top of the heat sink should be between −50° C. and 42° C., more preferably between 0° C. and 35° C., and even more preferably between 15° C. and 30° C. In another preferred embodiment, the temperature of the filament during FFF of P4HB and copolymers thereof at the bottom of the heat sink is between 15° C. and 42° C., more preferably between 20° C. and 35° C., and even more preferably between 25° C. and 32° C. In yet another preferred embodiment, the temperature of the filament during FFF of P4HB and copolymers thereof in the transition zone is between 15° C. and 100° C., more preferably between 30° C. and 95° C., and even more preferably between 42° C. and 92° C.

In an embodiment, the heat sink in the new equipment for FFF of P4HB and copolymers thereof is made from aluminum, and comprises fins that dissipate heat as shown in FIG. 2. The rate of cooling of P4HB and copolymer thereof may optionally be further increased by increasing the surface area of the heat sink, for example, by increasing the number of cooling fins, changing the thickness and size of the cooling fins, and increasing the length of the heat sink. In one embodiment, P4HB and copolymers thereof can be printed by FFF with a heat sink that is 29-36 mm in length and has a cross-sectional width of 15-17 mm, comprises cooling fins on 15-22 mm of its length that have a fin thickness of 1-2 mm, and has a cylindrical center with an inner diameter of 3-4 mm. While it is preferred that the compressed air, or other cooling gas, is directed at the lowest fin, compressed air, or other cooling gas, may alternatively be directed at different locations in the heat sink, or at multiple locations in the heat sink.

The rate of cooling of P4HB and copolymer thereof in the cold end may also be further adjusted by changing the pressure of the compressed air or gas directed at the heat sink of the FFF equipment. In an embodiment, the pressure of the compressed air or gas used to cool the heat sink is 0.1-100 psi (0.69-690 kPa), preferably 1-10 psi (6.9-69 kPa), and more preferably 7±1 psi (48.3±7 kPa).

The heat sink show in FIG. 2 may also be cooled by means other than the use of a compressed air or gas line focusing a stream of cooling air or gas on the bottom fin of the heat sink. In one alternative embodiment, the heat sink of the FFF equipment may be cooled by surrounding it on the outside with a jacket containing a cooling fluid. The cooling fluid is preferably cooled to maximize heat transfer from the heat sink to the cooling fluid, and is preferably circulated, even more preferably through a chiller. Suitable cooling fluids include water and mixtures of water with ethylene glycol, for example, a 70/30 ratio of water to ethylene glycol.

Maintenance of a low temperature in the cold end, to prevent the formation of soft plugs and softening of the filament of P4HB or copolymer thereof, can also be improved by increasing the distance in the transition zone between the heat sink and the heater block in the hot end of the FFF equipment. A longer distance decreases heat creep from the hot end to the cold end and improves printability of P4HB and copolymers thereof. In an embodiment, the length of the transition zone from the heat sink to the hot end is 1-8 mm, and more preferably 2-3 mm.

In a preferred embodiment, a shroud is attached to the print head so that the source of compressed air or gas moves with the print head during FFF of P4HB and copolymers thereof. The shroud is designed to ensure that the cooling air is directed at the heat sink. Concentrating the cooling air at the lowest region of the heat sink was found to be more effective at preventing heat creep from the hot end into the cold end than the use of diffuse air flow directed at the entire heat sink, for example, with a microblower shown in FIG. 1. In a preferred embodiment, the cooling compressed air or gas is directed at the lowest fin of the heat sink of the FFF equipment. The shroud is preferably made from a polymeric material. In an embodiment, the shroud shown in FIG. 2 comprises ABS.

In addition to preventing damage to the printed structure on the stage, the incorporation of a heat shield in the FFF equipment, shown in FIG. 2, prevents high pressure air or gas from cooling the heater block, and causing thermal errors of the printer hardware, heating failures, or terminating printing of P4HB and copolymers thereof. In one embodiment, the heat shield may comprise ABS.

Due to the high temperatures required for FFF printing of P4HB and copolymers thereof, it is desirable to incorporate an insulator between the hot end and the heat shield particularly when the glass transition temperature of the heat shield is low relative to the temperature in the hot end. This is the case when the heat shield is made from ABS. The ABS polymer has a glass transition temperature of 105° C. which means that a heat shield made from ABS would be deformed when the temperature in the hot end to print P4HB and copolymers thereof is 180-280° C. In one embodiment, the insulator that is placed between the heat shield and the hot end is made from silicon.

As described above, improved print quality is obtained when P4HB and copolymers thereof are printed by FFF on a stage with a very flat surface that can be cooled. In one embodiment, a stage with a very flat surface that can be cooled is made from aluminum. The aluminum stage results in improved print quality, particularly as a result of a substantial improvement in the quality of the first printed layer. Such an improvement prevents irregularities in the first print layer from being amplified in successive layers resulting in poor print quality during FFF of P4HB and copolymers thereof. Since P4HB and copolymers thereof are relatively slow to solidify, cooling increases the rate of solidification, and improves the adhesion of the first print layer as well as the adhesion of subsequent print layers that bind to the underlying hardening layer. In an embodiment, the temperature of the print stage for FFF of P4HB, copolymers and blends thereof is uniform across the stage, and is maintained in the range of 2-65° C., preferably 15-30° C., and even more preferably 18-25° C.

To print a high-quality object by FFF of P4HB and copolymers thereof, it is also important to control the distance between the printer nozzle and the top layer of the printed object. Optimization of this distance results in improved layer-to-layer adhesion. In an embodiment, the distance between the nozzle and the top layer of the object being printed should be 0.4-1.2 times the nozzle orifice diameter, more preferably 0.5-0.8 times the nozzle orifice diameter. For example, if the diameter of the nozzle orifice is 0.25 mm, the distance between the printer nozzle and the top layer of the object being printed would be 0.1-0.3 mm, and more preferably 0.125-0.2 mm.

B. Conditions for FFF of P4HB and Copolymers Thereof

In order to print P4HB and copolymers thereof by FFF using the equipment shown in FIG. 2, the quality of the filament and the processing conditions were also optimized. During processing of filaments of different diameters, filament diameter was found to be an important parameter in successful printing of filaments of P4HB and copolymers thereof. And in particular, the uniformity of filament diameter was found to be particularly critical. When the filament diameter was too small, printing was difficult because of the lack of traction of the driving gear on the filament. This resulted in insufficient force to drive the filament into the hot end. Conversely, if the diameter was too large, the filament would become jammed before entering the hot end. In an embodiment, the diameter of the filament of P4HB or copolymer thereof used in the FFF process should not be less than 80% of the diameter of the lumen of the heat sink or more than 94% of the diameter of the lumen of the heat sink.

In a preferred embodiment, the filament of P4HB or copolymer thereof used for FFF is prepared with a narrow diameter tolerance by pultrusion. Suitable filaments can be produced, for example, by cold pultrusion of P4HB and copolymers thereof using a pull force range of 4 to 7 kN, and a pull rate of 30-100 mm/s, and more preferably 40-60 mm/s.

A further problem with FFF of P4HB and copolymers thereof was discovered as a result of increasing the temperature in the hot end. At temperatures of 180-220° C. in the hot end, the P4HB polymer was still relatively viscous and print quality was not optimal. Increasing the temperature in the hot end up to about 280-290° C. was generally found to improve print quality as a result of lower viscosity of the polymer. However, when the temperature in the hot end was increased from 180° C. to 280° C., a more significant decrease in the weight average molecular weight (Mw) of the polymer was observed. In other words, improved print quality resulting from higher processing temperatures had the undesirable result of decreasing Mw leading to loss of polymer properties. Table 3 shows the loss of weight average molecular weight of a P4HB polymer with a Mw=374 kDa when it was printed at temperatures from 180° C. to 280° C. using the equipment set up shown in FIG. 2. At 180° C., there was a reduction in polymer weight average molecular weight of 30 kDa when the residence time was 104 s/mm$^3$. This increased to a reduction in polymer weight average molecular weight, for the same residence time, of 109 kDa at 280° C. representing a loss of about 30% of the polymer's weight average molecular weight. In a preferred embodiment, P4HB and copolymers thereof are printed by FFF in a temperature range of 180-280° C., more preferably 220-280° C., and even more preferably at 250-270° C. At the latter temperatures, good print quality was obtained with the least impact on weight average molecular weight reduction. In a preferred embodiment, objects comprising P4HB and copolymers thereof are printed by FFF with a reduction in Mw of the starting polymer of less than 25% using temperatures in the hot end of 180-270° C., and more preferably 220-270° C. In another preferred embodiment, P4HB and copolymers thereof printed by FFF have weight average molecular weights of 50-600 kDa, and more preferably 50-480 kDa.

TABLE 3

Decrease in P4HB weight average molecular weight during FFF as the nozzle temperature is increased with increased residence time

| | | Nozzle Temperature (° C.) | | | | | |
|---|---|---|---|---|---|---|---|
| | | 180 | 200 | 220 | 240 | 260 | 280 |
| Molecular weight Post Printing (kDa) | 52 s/mm$^3$ (Residence Time) | 315.5 | 361.3 | 361.0 | 352.7 | 335.6 | 318.7 |
| | 104 s/mm$^3$ (Residence Time) | 344.5 | 335.2 | 320.3 | 302.9 | 307.3 | 265.0 |
| | 208 s/mm$^3$ (Residence Time) | 295.9 | 287.9 | 331.5 | 333.7 | 287.6 | 201.0 |

The magnitude of the loss of polymer weight average molecular weight in FFF of P4HB and copolymers thereof does not only depend on the temperature in the hot end, but also depends on a number of other factors including nozzle geometry, dimensions of the heater block in the hot end, filament size, feed rate and the residence time. In an embodiment, the diameter of the nozzle orifice in the hot end is 0.1-1.2 mm, and more preferably 0.1-0.8 mm. At these diameters, good print quality is obtained with the least loss of Mw during printing. A non-limiting example of a heat block that can be used to print P4HB and copolymers thereof with good quality is one where the dimensions are 17 mm (width)×18 mm (length)×16 mm (height).

As shown in Table 3, it has been discovered that the loss of polymer weight average molecular weight that was found to occur when P4HB and copolymers thereof are printed by FFF can be reduced by minimizing the residence time of the polymer in the hot end. In an embodiment, the residence time is 10-1,000 s/mm$^3$, more preferably 40-500 s/mm$^3$, and even more preferably 50-110 s/mm$^3$. The reductions in weight average molecular weights shown in Table 3 at increasing nozzle temperatures were obtained using residence times of 52, 104, and 208 s/mm$^3$. In a preferred embodiment, P4HB and copolymers thereof are printed with a residence time between 52 and 208 s/mm$^3$ using a temperature in the hot end of 250-270° C.

In addition to all the factors described above, it was also found that the print quality during FFF of P4HB and copolymers thereof is also dependent on the filament feed rate. In one embodiment, filaments of P4HB and copolymers thereof are fed at a rate between 0.05 and 0.35 mm/s to produce a good quality object by FFF printing. In another embodiment, the filaments of P4HB and copolymers thereof are fed at a rate that allows good quality objects of P4HB and copolymers thereof to be produced by FFF with print speeds preferably of 2.5-7.5 mm/s. In one preferred embodiment, the filaments comprising P4HB and copolymers thereof are fed at a rate of 0.05-0.35 mm/s to produce objects by FFF using temperatures in the hot end of 220-280° C., and print speeds of 2.5-7.5 mm/s. In another preferred embodiment, the filaments comprising P4HB and copolymers thereof are fed at a rate of 0.22±0.05 mm/s to produce objects by FFF using temperatures in the hot end of 220-280° C., and print speeds of 5±0.1 mm/s. In a particularly preferred embodiment, the filaments comprising P4HB and copolymers thereof are fed at a rate of 0.22±0.05 mm/s to produce objects by FFF using temperatures in the hot end of 220-280° C., print speeds of 5±0.1 mm/s, and a residence time of 103±1 s/mm$^3$.

It should be noted that the preferred range of filament feed rates to obtain good quality P4HB prints depend on the geometry and size of the print nozzle used. The aforementioned preferred ranges correspond to nozzle diameter of 0.25 mm. Given the feed rate, nozzle size, and filament size, the aforementioned preferred ranges, correspond to a fluid shear rate at the nozzle ranging from 215 to 1500 sec$^{-1}$. For the preferred temperature ranges in the hot end of 220-270° C. and P4HB molecular weight range of 50-600 kDa, the polymer viscosity inside the nozzle at these shear rates ranges from 1200 to 4500 Pa-sec. In a preferred embodiment, polymer feed rates are adjusted when nozzle orifice diameters are 0.1 to 1.2 mm so that the shear rate at the nozzle ranges from 215 to 1500 sec$^{-1}$. For nozzle orifice diameters in the defined range of 0.1 to 1.2 mm, polymer feed rate ranges are adjusted such that the shear rate at the nozzle ranges in the preferred range of 215 to 1500 sec$^{-1}$.

In a preferred embodiment, the distance between the FFF print nozzle and either the surface of the print stage or the top of the highest printed layer is preferably 0.4-1.2 times the diameter of the orifice of the nozzle, more preferably between 0.5-0.8 times the diameter of the orifice of the nozzle. For example, the distance between the print nozzle and the top of the highest printed layer is preferably 0.1-0.3 mm, and more preferably 0.125-0.2 mm for a nozzle orifice with a diameter of 0.25 mm.

In a particularly preferred embodiment, the methods for FFF described herein allow the printing of objects of P4HB and copolymers thereof with a good print quality wherein the print dimensions are within 10% of the expected value. Thus, an object of P4HB or copolymer thereof produced by FFF, can be printed with an accuracy such that all dimensions of the object are printed within 10% of the target values for the object.

C. Other Equipment Modifications for FFF of P4HB and Copolymers Thereof

The equipment for FFF of P4HB and copolymers thereof may be further modified. In one embodiment, the FFF equipment may contain more than one print head. A multi-head printing system may be used, for example, to print a structure comprising P4HB and copolymers thereof with another material, such as another polymer, or to print a structure comprising P4HB and copolymers thereof with cells. In one embodiment, one print head can be used to create a porous structure comprising P4HB and copolymers thereof, and a second print head can be used to place cells in the pores of the structure of P4HB and copolymers thereof. In this manner, it is possible to create structures that can be used for tissue engineering applications.

D. Fused Pellet Deposition (FPD) of P4HB and Copolymers Thereof

Figure 8A:
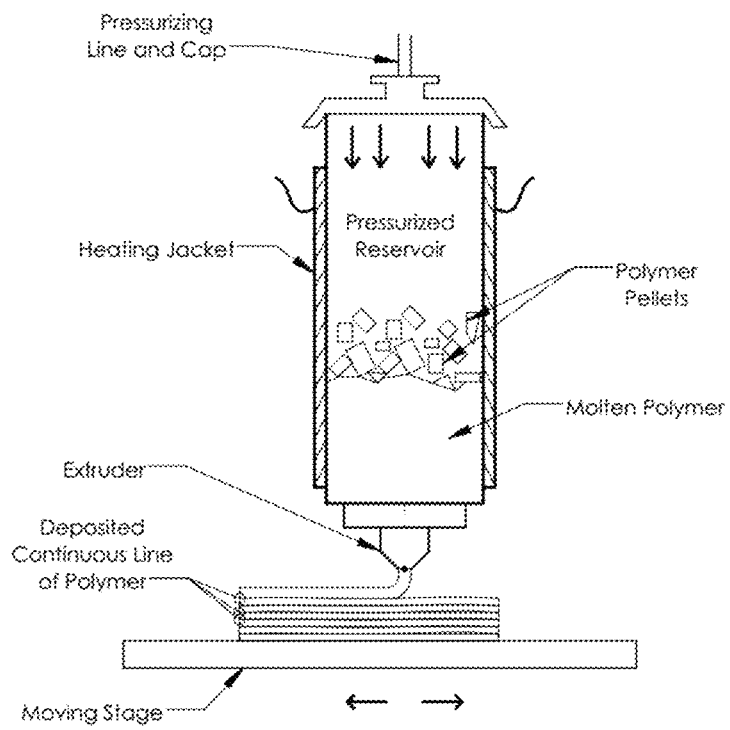
FIG. 8A is a diagram showing an equipment configuration for fused pellet deposition of P4HB and copolymers thereof.
Figure 8B:
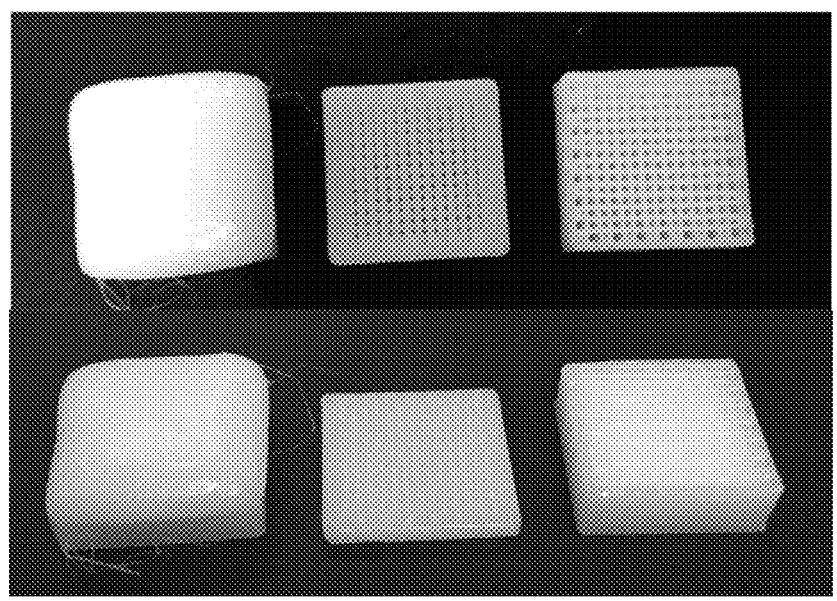
FIG. 8B is a picture showing products produced by fused pellet deposition of P4HB. The products shown on the left and in the middle position were warped and had poor print quality, and were produced with a processing temperature of 180° C. The product shown on the right had good resolution and print quality, and was printed with a processing temperature of 120° C.

FIG. 8A is a diagram showing an equipment set up suitable for 3D printing of P4HB and copolymers thereof by FPD. The equipment comprises a reservoir for polymer pellets that can be pressurized and is surrounded with a heating jacket, a cap fitting on one end of the reservoir with a compressed gas line that can be used to increase the pressure in the reservoir, and a nozzle located at the other end of the reservoir through which polymer can be printed onto a moving stage located underneath the nozzle. A computer programmed with 3D CAD data for the object to be printed is used to control the position of the stage and print head during printing. The diameter of the orifice of the nozzle is preferably 0.1 to 1.0 mm, and more preferably 0.15 to 0.4 mm. In a preferred embodiment, the P4HB or copolymer is dried prior to printing by FPD. P4HB and copolymers thereof can be FPD printed by charging the reservoir with polymer or copolymer pellets, sealing the reservoir with the cap and pressurizing the reservoir using compressed gas, preferably compressed air, and heating the reservoir. In an embodiment, the reservoir and pellets are heated to 85 to 180° C., more preferably 100 to 180° C., and even more preferably 120 to 150° C. In another embodiment, the reservoir is pressurized using dry compressed gas, preferably dry compressed air or nitrogen, to a pressure of 6.5-50 bars (650-5,000 kPa), and more preferably 9-20 bars (900-2,000 kPa). These conditions allow continuous 3D printing of P4HB and copolymers thereof by FPD. FIG. 8B (right picture) shows an object made from P4HB with good resolution by FPD using a processing temperature of 120° C. FIG. 8B (left and middle pictures) show a failed attempt to produce P4HB objects with good resolution at temperatures over 180° C.

In a particularly preferred embodiment, the methods for FPD described herein allow the printing of objects of P4HB and copolymers thereof with a good print quality wherein the print dimensions are within 10% of the expected value. That is, each dimension of the object is within ±10% of the target value.

E. Melt Extrusion Deposition (MED) of P4HB and Copolymers Thereof

Figure 9A:
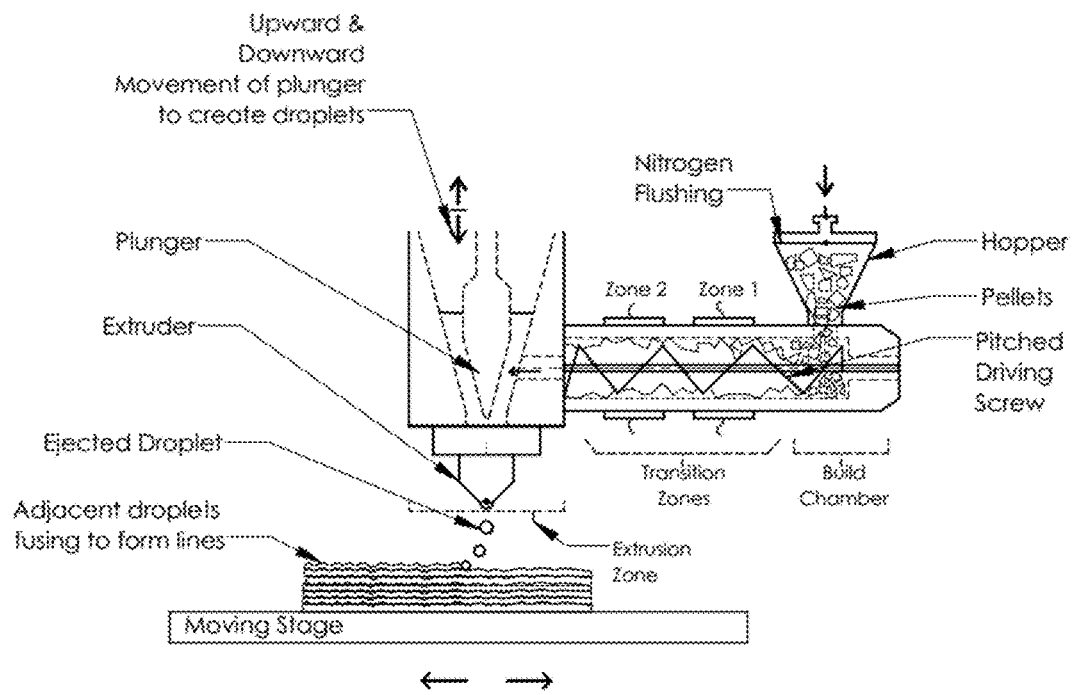
FIG. 9A is a diagram showing a suitable equipment set up for melt extrusion deposition (MED) of P4HB and copolymers thereof.

FIG. 9A is a diagram showing an equipment set up that can be used for 3D printing of P4HB and copolymers thereof by MED. The equipment set up comprises a horizontal single screw heated barrel with a hopper for the polymer that is designed to protect the polymer from moisture. The hopper is designed to exclude moisture from the polymer in the hopper in order to prevent loss of polymer molecular weight during printing. The hopper is fitted with a dry gas purge, preferably a nitrogen purge to keep the polymer dry. The horizontal extruder is connected to a vertical extruder fitted with a plunger so that polymer can be moved through the horizontal extruder into the vertical extruder. The vertical extruder is fitted with a plunger that is used to eject the polymer as small droplets through a nozzle orifice. The plunger creates the small droplets of molten polymer with a hammer-like action. Preferably the plunger is piezoelectrically driven to create the droplets of polymer. The droplets are collected on a moving stage, and fuse upon contact to form a polymer print line. That is, the print line is formed by the ejection of a series of drops which fuse together to form the print line as shown in FIG. 9A. A computer programmed with 3D CAD data for the object to be printed is used to control the position of the stage during printing.

In a preferred embodiment, pellets of P4HB or copolymer thereof suitable for MED printing are prepared with diameters of 0.05-3 mm, and more preferably 1-3 mm. In order to avoid a significant loss in molecular weight of the polymer or copolymer during processing, it is important that the polymer or copolymer thereof is dried prior to MED printing so that the water content of the polymer or copolymer is less than 1,000 ppm, more preferably less than 500 ppm, and even more preferably 10-300 ppm. In a preferred embodiment, the temperature profile of the MED's horizontal extruder is set: between 20 and 60° C. in the build chamber and more preferably between 25 and 40° C.; between 60 and 150° C. in the heating zones, and more preferably between 90 and 140° C.; and between 150° C. and 250° C. in the extrusion zone, and more preferably between 190° C. and 230° C. The back pressure applied to the molten polymer ranges from 5 to 100 bars (0.5-10 MPa), and more preferably between 20 and 70 bars (2-7 MPa), and even more preferably between 40 and 60 bars (4-6 MPa).

The residence time of the polymer or copolymer in the MED's horizontal extruder is preferably 0.1 to 10 sec/mm$^3$, and more preferably 1 sec/cm$^3$ to 7 sec/mm$^3$. And, preferably the diameter of the nozzle orifice of the vertical extruder for producing a good print quality is from 0.08 to 0.4 mm, more preferably 0.15 to 0.2 mm. These conditions allow objects with good print quality to be produced by MED from P4HB and copolymers thereof.

In a particularly preferred embodiment, the methods for MED described herein allow the printing of objects of P4HB and copolymers thereof with a good print quality wherein the print dimensions are within 10% of the expected value. That is, each dimension of the object is within ±10% of the target value.

F. Selective Laser Melting (SLM) of P4HB and Copolymers Thereof

Figure 10:
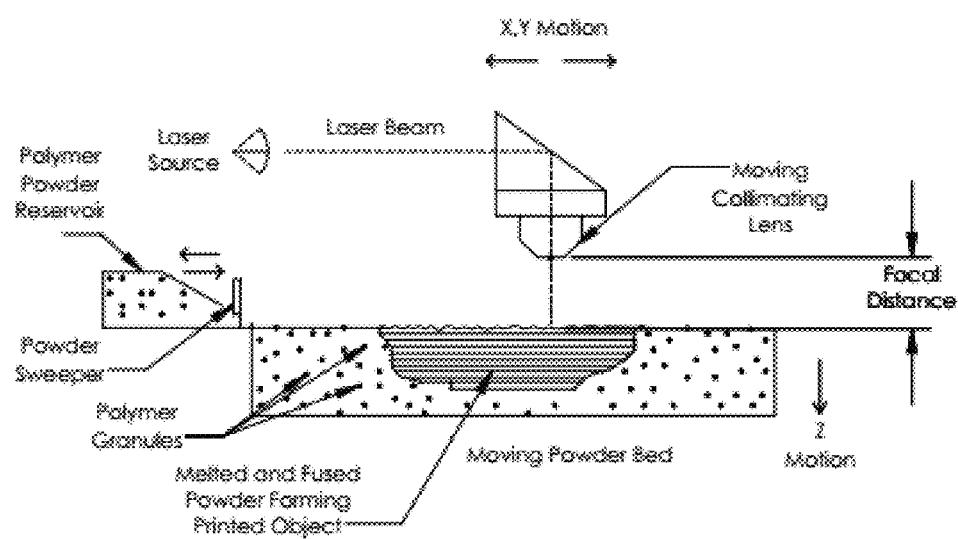
FIG. 10 is a diagram showing a suitable equipment set up to 3D print objects from P4HB and copolymers thereof by selective laser melting (SLM).

FIG. 10 is a diagram showing an equipment set up that is designed for 3D printing of P4HB and copolymers thereof by SLM. The equipment set up comprises a moving powder bed, a polymer powder reservoir and powder sweeper, and a laser source and moving lens that can be used to focus a laser on the polymer in the powder bed. The lens is able to move in the X and Y directions. A computer programmed with 3D CAD data for the object to be printed is used to control the positions of the powder bed and laser beam, and the movement of the powder sweeper. P4HB and copolymers thereof can be 3D printed by using the laser to selectively fuse the powder, and an object is printed by scanning the laser across the surface of the powder in X and Y directions in a pattern controlled by the computer. Preferably, the laser is a high-powered CO$_2$ laser. The equipment set up allows objects comprising P4HB and copolymers thereof to be built one layer at a time into a 3D object. After a layer is printed, the polymer bed is lowered (in the Z direction shown in FIG. 10), fresh polymer powder is spread across the print surface, and the surface is then swept with the powder sweeper to produce a uniform thickness of polymer powder ready for printing the next layer.

Several parameters critical to successful printing of P4HB and copolymers by SLM have been discovered. These are the laser power, the speed of movement of the laser across the powder bed, the particle size of the powder, and the thickness of the layer of powder. In a preferred embodiment, objects comprising P4HB and copolymers thereof are printed by SLM from granules with average particle sizes ranging from 0.5 to 200 µm, more preferably 5 to 120 µm, and even more preferably 20 to 50 µm. In a particularly preferred embodiment, the granules comprising P4HB and copolymers thereof have particle sizes that are no more than 25% larger or smaller than the average particle sizes, and more preferably have particle sizes that are no more than 10% larger or smaller than the average particle sizes. Thus, the granules of P4HB and copolymers thereof should not be larger than 250 µm and not smaller than 0.375 µm, are more preferably sized between 3.75 µm and 150 µm, and even more preferably are sized between 15 µm and 62.5 µm. In a particularly preferred embodiment, the granules of P4HB and copolymers thereof used for SLM printing are prepared by cryo-milling. This method is preferred because of the ductility of P4HB and copolymers thereof, which makes processes such as ball milling unsuitable for preparing the granules for SLM. Cryo-milling of P4HB and copolymers thereof is preferably performed by cooling the polymer or copolymer to a temperature below its glass transition temperature, preferably with liquid nitrogen, and then grinding to form granules. In another preferred embodiment, the granules are sieved to provide the desired particle sizes described herein. Granules of P4HB and copolymers thereof with weight average molecular weights from 80 to 1,000 kDa have been found to be particularly suitable for 3D printing by SLM. Objects made from P4HB and copolymers thereof with Mw of 80-200 kDa are particularly suitable for preparing absorbable implants where it is desirable for the implant to degrade in 4-12 weeks, while objects made from P4HB and copolymers thereof with Mw of 201-800 kDa are suitable for preparing absorbable implants where it is desirable for the implant to degrade in 3-12 months.

Figure 11A:
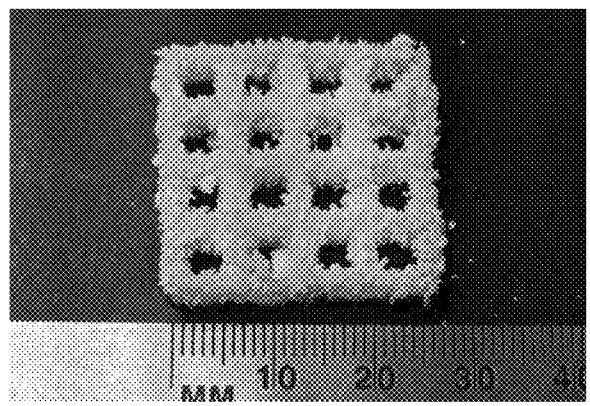
FIG. 11A is a picture of a P4HB lattice printed by SLM.
Figure 11B:
FIG. 11B is a picture showing the result of a failed attempt to print a P4HB lattice by SLM.

In an embodiment, objects comprising P4HB and copolymers thereof are printed by SLM by spreading and sweeping the powder on the moving bed prior to printing each layer so that the thickness of the powder ranges from 5 to 250 µm. More preferably the thickness of the powder spread on the moving bed prior to printing matches the focal length of the collimating lens of the laser. After spreading the powder, the laser beam is moved in the X and Y directions to melt and fuse the polymer, and form a layer of the object. In an embodiment, the laser power for SLM of P4HB and copolymers thereof is preferably from 0.06 to 60 Watts. At lower laser power, SLM of P4HB results in poor adherence of the powder particles, and the formation of crumbles of polymer as shown in FIG. 11B. At laser power higher than 60 Watts, SLM of P4HB results in excess melting of the polymer, decreased weight average molecular weight, and very poor print resolution with adjacent print lines even fusing to one another. In another embodiment, the speed of movement of the laser beam on the powder bed is preferably from 0.1 to 40 cm/s. This range of speed in combination with the preferred range of laser power allows proper melting of the polymer and fusion of the P4HB particles to form objects with good print quality. The selection of the power and speed should be such that the ratio of the power to speed times width of the printed line (ranging typically between 100 and 200 microns) ranges between 0.5 to 10 $J/cm^2$, preferably between 0.8 and 5 $J/cm^2$, and even more preferable between 0.9 and 1.5 $J/cm^2$.

In a particularly preferred embodiment, the methods for SLM described herein allow the printing of objects of P4HB and copolymers thereof with a good print quality wherein the print dimensions are within 25% of the expected value. That is, each dimension of the objected is within ±25% of the target value.

G. 3D Solution Printing of P4HB and Copolymers Thereof by Coagulation Method

Figure 12:
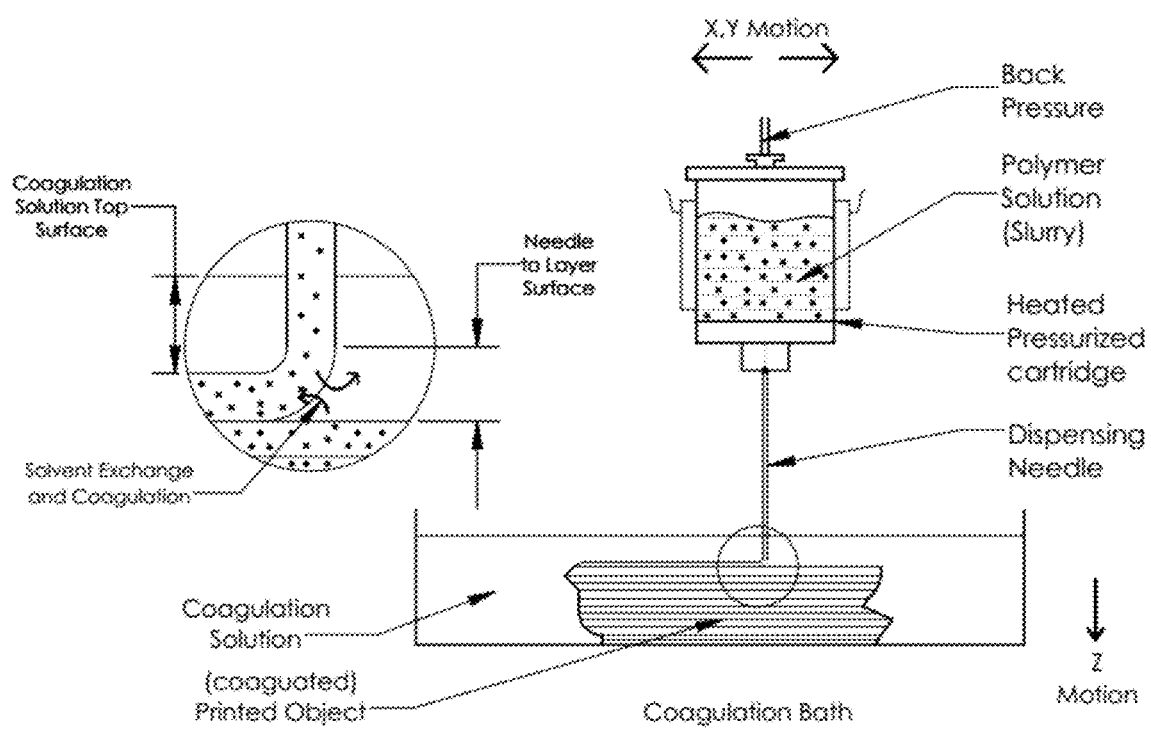
FIG. 12 is a diagram showing a suitable equipment set up to print objects from solutions or slurries of P4HB and copolymers thereof by 3D printing using a coagulation bath.

FIG. 12 is a diagram showing an equipment set up that is designed for 3D solution printing of P4HB and copolymers thereof using a coagulation bath. The equipment set up comprises a pressurized dispenser containing a solution or slurry of P4HB or copolymer thereof with a dispensing needle, and a movable coagulation bath. The dispenser can be pressurized and heated, and is designed to dispense a polymer solution into the coagulation bath to form a 3D printed object. A computer programmed with 3D CAD data for the object to be printed is used to control the positions of the dispensing needle and the coagulation bath. The computer can move the dispensing needle in the X and Y directions, and the coagulation bath in the Z direction (i.e. upward or downward), or alternatively, the computer can move the dispensing needle in all directions (i.e. X, Y and Z). The coagulation bath is filled with a coagulation solution.

In a preferred embodiment, the solution or slurry of P4HB or copolymer thereof is dissolved or suspended in a solvent, preferably acetone. In a particularly preferred embodiment, the P4HB or copolymer thereof is dissolved or suspended in acetone at a concentration of 0.05 to 6% w/v. In alternative embodiments, the P4HB or copolymer thereof may be dissolved or suspended in chloroform, dioxane or tetrahydrofuran. The concentration of P4HB or copolymer thereof in: (i) chloroform is preferably 0.05 to 10% w/v, (ii) dioxane is preferably 0.05 to 8% w/v, and (iii) tetrahydrofuran is preferably 0.05 to 10% w/v. The solution or slurry of P4HB or copolymer thereof may be heated prior to printing. Preferably the solution or slurry of P4HB in acetone is heated to a temperature from 40 to 50° C., and more preferably from 42° C. to 49° C. To obtain good print quality, the inner diameter of the dispensing needle is preferably 15 µm to 1.2 mm. The back pressure from the pressurized dispenser is preferably between 1.5 to 8 bars (150 to 800 kPa).

It has been discovered that the choice of coagulation solvent in the coagulation bath is critical for successful printing of P4HB and copolymers thereof. The coagulation solvent must be miscible with the solvent used to prepare the polymer solution or slurry, and it must be able to cause phase separation. That is, contact of the coagulation solvent with the solvent used to prepare the solution or slurry of P4HB or copolymer thereof must result in diffusion of the latter solvent away from the polymer or copolymer in the coagulation bath, and coagulation to form the 3D printed object. In a preferred embodiment, the solvent in the coagulation bath is stirred in order to obtain good mixing of the polymer solvent and the coagulation solvent. Preferred combinations of solvents used for 3D solution printing of P4HB and copolymers thereof, including preferred concentrations, are shown in Table 4. The listed solvents may also be used in combination. For example, mixtures of methanol and ethanol, methanol and water, ethanol and water, or methanol, ethanol and water, may be used as the coagulation solvent.

TABLE 4

Solvent combinations for 3D solution printing of P4HB and Copolymers Thereof

| Solvent used in slurry | Concentration of polymer/copolymer in slurry | | Coagulation solvent |
|---|---|---|---|
| | Range (w/v) | Preferred (w/v) | |
| Chloroform | 0.05-10% | 5-8% | Methanol, Ethanol |
| Acetone | 0.05-6% | 2-5% | Water, Ethanol, Methanol |
| Dioxane | 0.05-8% | 3-6% | Water, Ethanol, Methanol |
| Tetrahydrofuran (THF) | 0.05-10% | 5-8% | Water, Ethanol, Methanol |

Figure 13:
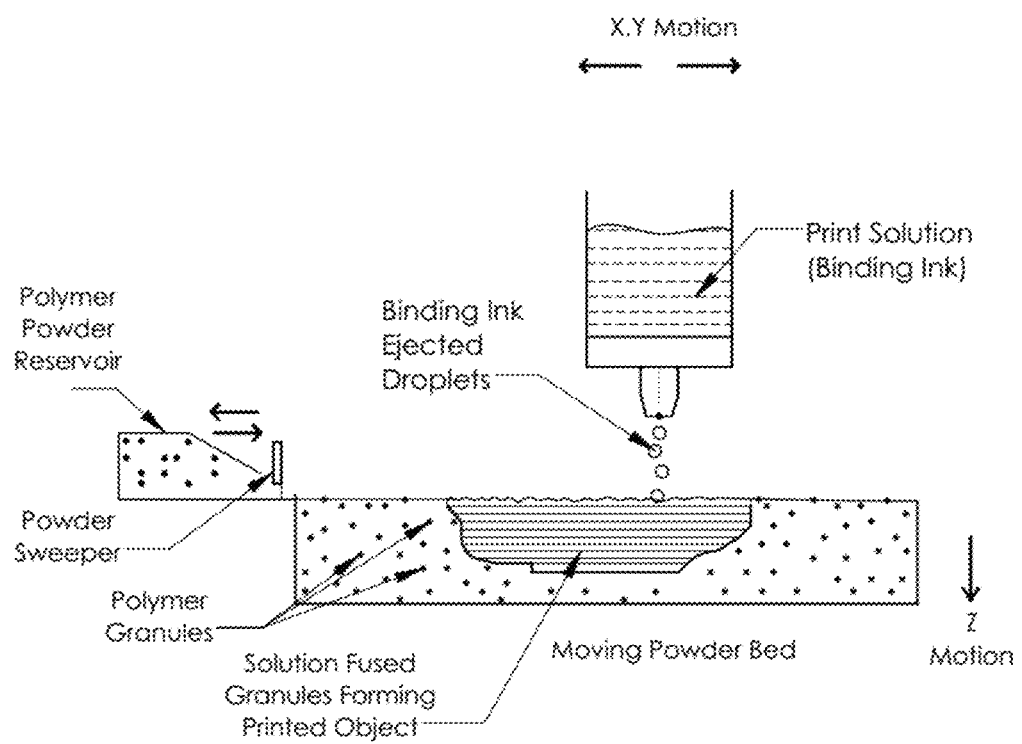
FIG. 13 is a diagram showing a suitable equipment set up to print objects from P4HB and copolymers thereof using a binding solution and granules of polymer or copolymer on a moving bed.

H. 3D Printing of P4HB and Copolymers Thereof using a Binding Ink and Granules of Polymer or Copolymer FIG. 13 is a diagram showing an equipment set up that is designed for 3D printing of P4HB and copolymers thereof. The equipment set up comprises a reservoir for a binding ink that can eject droplets of the ink onto a moving powder bed fitted with a polymer powder reservoir and a powder sweeper. A computer programmed with 3D CAD data for the object to be printed is used to control the positions of the ejected droplets of ink, and the moving powder bed. Preferably, the computer can move the former in the X and Y directions, and the latter in the Z direction (as shown in FIG. 13). Alternatively, the computer can move the droplet ejector in all directions (i.e. X, Y and Z directions). P4HB and copolymers thereof can be 3D printed by using the binding ink to fuse the polymer powder. An object comprising P4HB and copolymers thereof is printed by depositing the droplets of binding ink across the surface of a layer of powder in X and Y directions in a pattern controlled by the computer. The printing ink causes the powder comprising P4HB or copolymers thereof to fuse. After a layer is printed, the polymer bed is lowered (in the Z direction shown in FIG. 13), fresh polymer powder is spread across the print surface, and the surface is then swept with the powder sweeper to produce a uniform thickness of polymer powder ready for printing the next layer.

In a preferred embodiment, 3D objects of P4HB and copolymers thereof are formed by printing from granules of powder with average sizes ranging from 0.5 to 250 μm, more preferably 1 to 100 μm, and even more preferably 5 to 50 μm. In a particularly preferred embodiment, the granules comprising P4HB and copolymers thereof have particle sizes that are no more than 25% larger or smaller than the average particle sizes, and more preferably have particle sizes that are no more than 10% larger or smaller than the average particle sizes. Thus, the granules of P4HB and copolymers thereof for 3D printing should not be larger than 312.5 μm and not smaller than 0.375 μm, are more preferably sized between 0.75 μm and 125 μm, and even more preferably are sized between 3.75 μm and 62.5 μm. In a particularly preferred embodiment, the granules of P4HB and copolymers thereof for 3D printing are prepared by cryo-milling as described herein. In another preferred embodiment, the granules are sieved to provide the desired particle sizes described herein. Granules of P4HB and copolymers thereof with weight average molecular weights from 80 to 500 kDa are particularly suitable for 3D printing with binding inks. Objects made from P4HB and copolymers thereof with Mw of 80-200 kDa are particularly suitable for preparing absorbable implants where it is desirable for the implant to degrade in 4-12 weeks, while objects made from P4HB and copolymers thereof with Mw of 201-800 kDa are suitable for preparing absorbable implants where it is desirable for the implant to degrade in 3-12 months.

In an embodiment, 3D objects comprising P4HB and copolymers thereof are printed with the binding inks by spreading the powder on the moving bed prior to printing each layer so that the thickness of the powder ranges from 50 to 250 μm. After spreading the powder, ejected droplets of binder ink are moved in the X and Y directions to fuse adjacent granules of P4HB or copolymer thereof. Preferred binding inks for preparing 3D printed objects of P4HB and copolymers thereof include chloroform, acetone, tetrahydrofuran and dioxane.

In an embodiment, drop-on-demand (DOD) inkjet printers (piezo or bubble jet) with solvent resistant cartridges, heaters and piezo-elements can be used to 3D print P4HB and copolymers thereof using binding inks and granules of polymer or copolymer as described herein.

IV. Medical Implants Produced by 3D Printing of Compositions Comprising P4HB and Copolymers Thereof The ability to 3D print compositions comprising P4HB and copolymers thereof makes it possible to rapidly fabricate objects that can be used as implants, implant prototypes, or parts of implants, without preparing expensive custom molds. The new methods also make it possible to commercially produce objects that can be used as implants that are difficult to produce by alternative processing methods, or are more expensive to produce by alternative processing methods. For example, an implant may have geometries that are difficult or impossible to produce by standard machining, but that can be readily produced by 3D printing. An example is an implant with multilevel fluidic channels.

Objects made from P4HB and copolymers thereof with Mw of 80-200 kDa are particularly suitable for preparing absorbable implants where it is desirable for the implant to degrade in 4-12 weeks, while objects made from P4HB and copolymers thereof with Mw of 201-800 kDa are suitable for preparing absorbable implants where it is desirable for the implant to degrade in 3-12 months.

Implants, and components of implants, made by 3D printing of compositions comprising P4HB and copolymers thereof may be used for soft and hard tissue repair, regeneration, and replacement. The methods described herein may be used to produce implants comprising P4HB and copolymers thereof, including the following types of implants: mesh, mesh suture, tube, catheter, monofilament mesh, multifilament mesh, wound healing device, bandage, wound dressing, burn dressing, ulcer dressing, skin substitute, hemostat, tracheal reconstruction device, organ salvage device, dura substitute, dura patch, nerve guide, nerve regeneration or repair device, hernia repair device, including hernia mesh, hernia plug, and devices for repair of ventral, inguinal, femoral, umbilical, incisional, epigastric and hiatal hernias, device for temporary wound or tissue support, tissue engineering scaffold, guided tissue repair/regeneration device, anti-adhesion membrane, adhesion barrier, tissue separation membrane, retention membrane, sling, device for pelvic floor reconstruction, urethral suspension device, device for treatment of urinary incontinence, including stress urinary incontinence, device for treatment of vesicoureteral reflux, bladder repair device, sphincter muscle repair device, bulking or filling device, bone marrow scaffold, clip, clamp, screw, pin, nail, medullary cavity nail, bone plate, interference screw, tack, fastener, rivet, staple, fixation device for an implant, bone graft substitute, bone void filler, suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, osteochondral repair device, spinal fusion device, mandibular device, cranial bone void device, maxilla implant device, craniomaxillofacial device, device for treatment of osteoarthritis, viscosupplement, stent, including coronary, cardiovascular, peripheral, ureteric, urethral, urology, gastroenterology, nasal, ocular, or neurology stents and stent coatings, stent graft, cardiovascular patch, catheter balloon, vascular closure device, intracardiac septal defect repair device, including but not limited to atrial septal defect repair devices and PFO (patent foramen ovale) closure devices, left atrial appendage (LAA) closure device, pericardial patch, vein valve, heart valve, vascular graft, myocardial regeneration device, periodontal mesh, guided tissue regeneration membrane for periodontal tissue, dental bone void filler, ocular cell implant, imaging device, cochlear implant, embolization device, anastomosis device, cell seeded device, cell encapsulation device, controlled release device, drug delivery device, plastic surgery device, breast lift device, mastopexy device, breast reconstruction device, breast augmentation device (including devices for use with breast implants), breast reduction device (including devices for removal, reshaping and reorienting breast tissue), devices for breast reconstruction following mastectomy with or without breast implants, facial reconstructive device, forehead lift device, brow lift device, eyelid lift device, face lift device, tummy tuck device, arm lift device, rhytidectomy device, rhinoplasty device, device for malar augmentation, otoplasty device, neck lift device, mentoplasty device, cosmetic repair device, device for facial scar revision, and enclosure, pouch, holder, cover, and clamshell casings to hold implantable medical devices, including pacemakers. The implants may further comprise nucleants, plasticizers, ceramics, bioceramics, bioactive agents including antibiotics, contrast agent, radiopaque and/or radioactive substances.

The implants described herein have substantially improved properties for many medical applications. In particular, these implants can be produced with lower levels of organic impurities, inorganic impurities, and residual solvents that can react with the body upon implantation. The low levels of these impurities will reduce or minimize undesirable reactions such as inflammation, cytotoxicity, irritation, pyrogenicity, subchronic and chronic toxicity. Devices made from or including P4HB and copolymers thereof may be prepared with endotoxin contents of less than 20 endotoxin units per device.

The implants made by 3D printing of P4HB and copolymers thereof may be sterilized using ethylene oxide gas, and even more preferably using an ethylene oxide cold cycle. In another embodiment, the implants may be sterilized with electron-beam irradiation or gamma-irradiation. In yet another embodiment, the implants may be sterilized using alcohol. The sterility of the implants may be maintained by packaging of the implants in packages designed to protect the implants from contamination and maintain sterility.

The present invention will be further understood by reference to the following non-limiting examples.

Comparative Example 1: Attempted 3D Printing of P4HB by FFF

Figure 3:
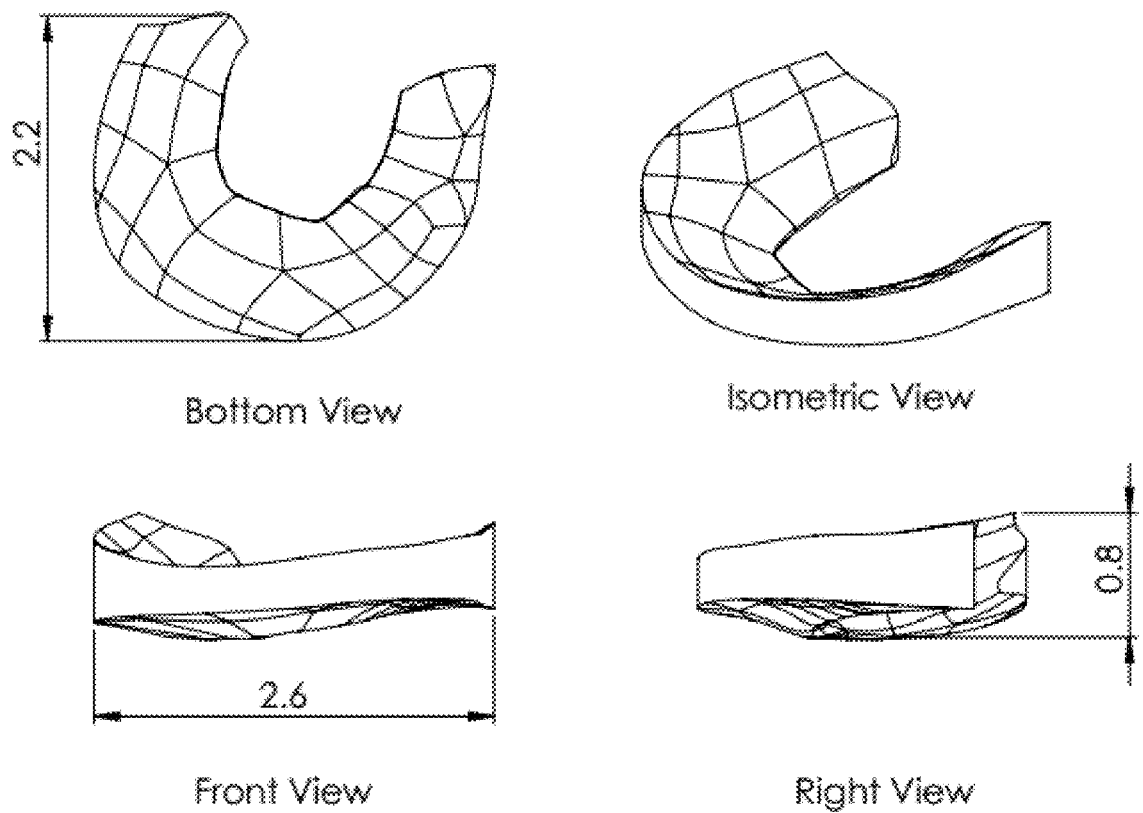
FIG. 3 is a diagram showing the bottom view, front view, isometric view and right view of a meniscal implant with dimensions of 2.6 cm width, 2.2 cm length, and 0.8 cm height.

An attempt was made to print a meniscal implant shown in FIG. 3 with P4HB filament using a commercial LulzBot Taz 6 3D printer. The dimensions of the desired meniscal implant were approximately 2.6 cm wide by 2.2 cm long and 0.8 cm high with a square fill pattern having a square pore size of 0.5 mm×0.5 mm. The printer was equipped with a standard 3 mm filament feeder, 0.25 mm nozzle, a 20 cfm micro-blower, and a heated printing stage. An STL (stereolithography) file was created for the meniscal implant, and rendered into a 3D printing profile (Matter Control) consisting of 42 slices (layers) with a height of 0.2 mm each (see FIG. 4). The P4HB filament used for printing had a Mw of 340 kDa and an average diameter of 2.95 mm. A filament feed rate of 0.22 mm/s was used. The temperature in the hot end was set to 220° C., and the print speed set at 6.5 mm/s. The temperature of the printing stage was set to 30° C. The temperature during printing at the top of the transition zone was 60° C. and the temperature at the top of the heat sink was 56.5° C. To allow fusion of the first printed layer to the print stage, the print head was offset by 0.15 mm. The layer (slice) thickness was set to 0.2 mm to allow for the subsequent build and proper fusion of the stacked layers. Based on these conditions, it was estimated that printing of the meniscal implant would require 1 hour and 15 mins. However, printing failed within 10-15 mins due to failure of filament feeding. A picture of the object produced during this time is shown in FIG. 5. Additionally, the weight average molecular weight of the printed P4HB structure shown in FIG. 5 was determined, and found to be only 200 kDa indicating a massive drop (140 kDa) in the weight average molecular weight of the polymer during printing.

Example 1: Successful 3D Printing of a P4HB Meniscal Implant by FFF

In this example, the same setup parameters were used as in Comparative Example 1 above. However, multiple modifications were made to the 3D printer as follows. A shroud was attached to the printer head which incorporated a compressed air line and nozzle to focus cooling air on the lowest fin of the heat sink. A heat shield was located in the transition zone between the hot end and the heat sink to prevent the compressed air from hitting the hot end and printing stage. An insulator, made from silicon, was located between the hot end and the heat shield to protect the heat shield from thermal deformation. And, the printing stage was replaced with an aluminum stage that could be cooled, and that had a flatter surface. The stage was maintained at 22° C. during printing. The modified equipment set up is shown in FIG. 2.

P4HB filament with an average diameter of 2.85 mm, and a polymer Mw of 340 kDa, was used for printing. Directing compressed air at a temperature of 18° C., and at a rate of 2,400 cfm (67.2 m³/min), to the lowest fin of the heat sink resulted in a significant temperature drop at the top of the transition zone and the top of the heat sink. The temperature at the top of the transition zone was lowered to 30.5° C. (from 60° C. in Comparative Example 1), and the temperature at the top of the heat sink was lowered to 28.5° C. (from 56.5° C. in Comparative Example 1). As in Comparative Example 1, the layer (slice) thickness was set to 0.2 mm to allow for the subsequent build and proper fusion of stacked layers.

Figure 4:
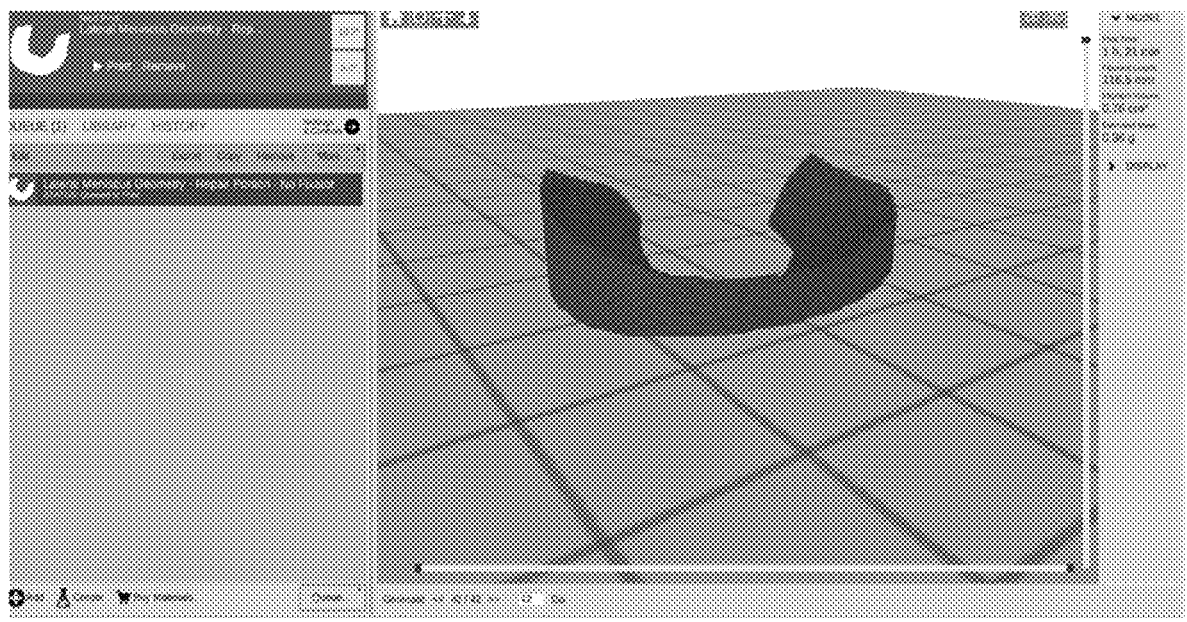
FIG. 4 is a 3D printing profile for the meniscal implant shown in FIG. 3 consisting of 42 slices (layers) with a height of 0.2 mm each.
Figure 5:
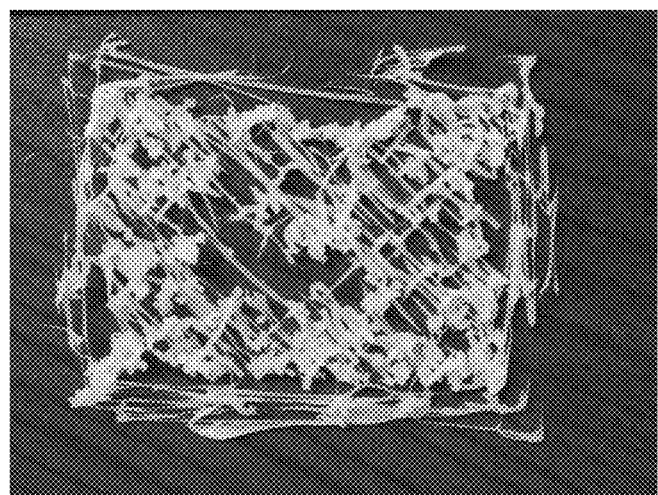
FIG. 5 is a picture showing the failed result of an attempt to print the meniscal implant with the 3D printing profile shown in FIG. 4 with P4HB filament using a standard commercial FFF 3D printer.
Figure 6:
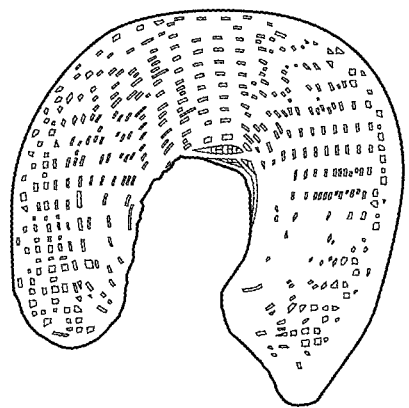
FIG. 6 is a picture of a meniscal implant successfully printed by FFF from P4HB filament using the customized 3D printer shown in FIG. 2 and the 3D printing profile shown in FIG. 4.

Using the equipment shown in FIG. 2, and the conditions described, the meniscal implant shown in FIG. 6 was successfully prepared using the STL file created in Comparative Example 1 (see FIG. 4). The Mw of the printed polymer object show in FIG. 6 was determined, and found to be 250 kDa, representing a drop in Mw of 26.5% during printing. The decrease in Mw during printing was significantly less than that observed in Comparative Example 1. Importantly, the meniscal implant shown in FIG. 6 was produced by continuous printing that lasted 1 hour 21 min, and was not interrupted, demonstrating a robust process for continuous 3D printing of P4HB and copolymers thereof.

Example 2: 3D Printing of a P4HB Mesh by FFF

Figure 7A:
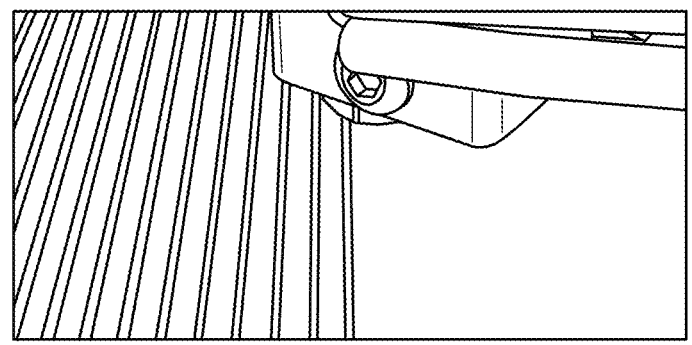
FIG. 7A is a picture showing continuous FFF of a P4HB mesh and good adhesion of the first layer to the stage.
Figure 7B:
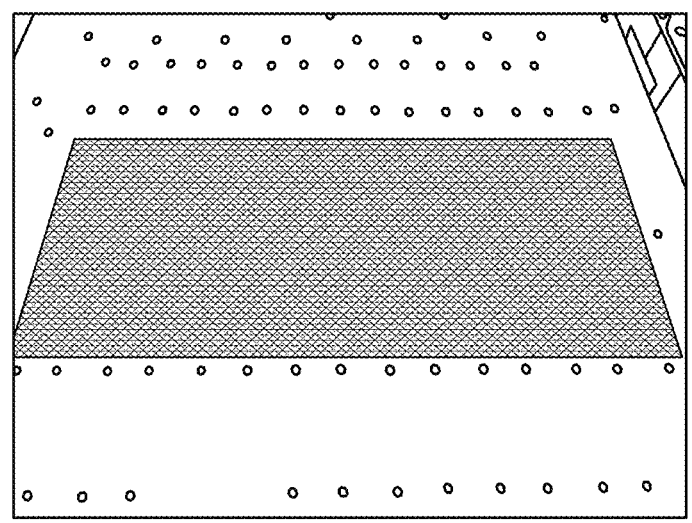
FIG. 7B is a picture of a P4HB mesh with a crisscross pattern printed by FFF on a level aluminum stage.
Figure 7C:
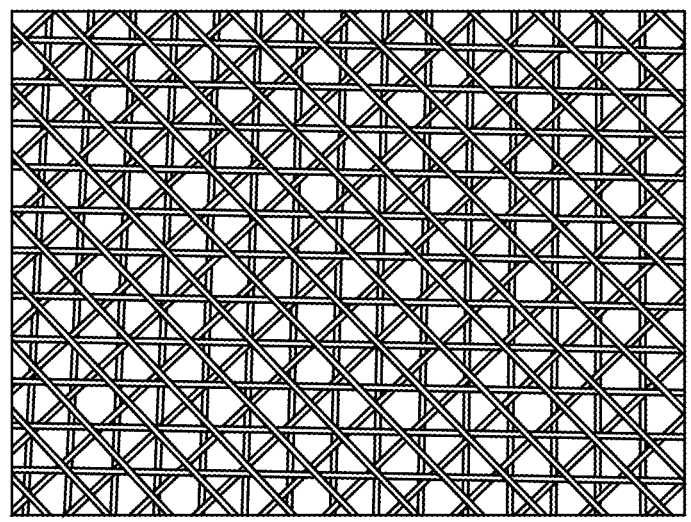
FIG. 7C is a picture showing a close-up view of the crisscross pattern of a P4HB mesh printed by FFF.

A P4HB mesh with a crisscross pattern was printed with the FFF 3D printer set up shown in FIG. 2 using the following method. The desired crisscross pattern, with a line to line distance of 2 mm and consecutive layers set at 45 degrees to each other, was transformed into an STL file, and rendered into a two-slice 3D printing profile (Matter Control) with a slice (layer) height of 0.25 mm. Unoriented P4HB monofilament (Mw=340 kDa) with an average diameter of 2.85 mm was fed into the printer at a feed rate of 0.22 mm/s, heated in the hot end to a temperature of 270° C., and printed from a nozzle with an orifice diameter of 0.3 mm and a print speed of 6.5 mm/s. The stage was made from aluminum, and was maintained at a temperature of 22° C. during printing. Adhesion of the first printed layer to the aluminum stage was excellent, and very uniform as shown in FIG. 7A. The temperature at the bottom of the heat sink was maintained at 30° C. by directing compressed air at a pressure of 2 psi (13.8 kPa) at the bottom of the heat sink (as shown in FIG. 2). Under these conditions, the temperature at the top of the heat sink was 28° C. Excellent fusion of consecutive layers occurred when the distance from the print head to the top of the most recently printed layer was 0.25 mm. The printing of the mesh was completed with no interruptions, and resulted in a mesh with a good print quality as shown in FIG. 7B, and the close-up view of the printed mesh shown in FIG. 7C. The 3D printed P4HB mesh had an average density of 284 g/m$^2$, a thickness of 1.1 mm, and very good print quality with print dimensions that were within 3% of the expected values.

Example 3: 3D Printing of P4HB by Fused Pellet Deposition (FPD)

A P4HB object was printed by FPD using the equipment set up shown in FIG. 8A comprising a reservoir with a heated jacket and a pressure line and cap, a nozzle located at the bottom of the reservoir, and a moving stage. The reservoir was charged with P4HB pellets (Mw 150 kDa), pressurized with compressed air to a pressure of 9 bars (900 kPa), and the pellets were heated to 120° C. Under these conditions, it was possible to print good quality objects comprising P4HB when the diameter of the orifice in the printer nozzle was 0.2 mm (FIG. 8B; right). When the temperature exceeded 180° C., the printed structure warped and had poor resolution (FIG. 8B; middle and left).

Comparative Example 3: Attempted 3D Printing of P4HB by Fused Pellet Deposition (FPD)

An attempt was made to 3D print objects from P4HB (Mw 150 kDa) using the equipment set up shown in FIG. 8A using a pressure of 9 bars (900 kPa), and heating the pellets to temperatures above 180° C. At these higher temperatures, it was not possible to print good quality objects comprising P4HB. Printing at these higher temperatures resulted in objects with poor resolution and significant warping as shown in FIG. 8B; middle and left pictures.

Example 4: 3D Printing of P4HB by Melt Extrusion Deposition (MED)

Figure 9B:
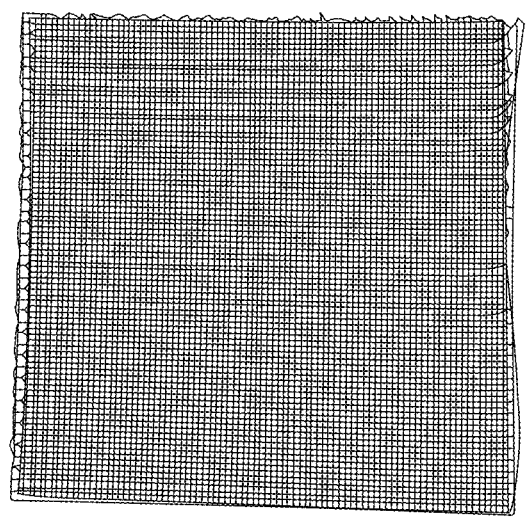
FIG. 9B is an example of a P4HB product printed by melt extrusion deposition (MED) with good print quality.

A P4HB object was printed by MED using the equipment set up shown in FIG. 9A comprising a horizontal extruder feeding into a vertical extruder fitted with a vertical plunger, and a movable stage. The extruder hopper was charged with P4HB pellets (480 kDa) with a diameter of 3.3 mm and moisture content of 18 ppm. The pellets were kept dry in the hopper using a purge of air dried through a silica bed. The temperature profile of the horizontal extruder was set to 30° C. in the build chamber; 100° C. in the transition zone 1, 130° C. in zone 2; and 230° C. in the extrusion zone. The residence time of the polymer in the MED horizontal extruder was 22 min/cm$^3$. The back pressure was set to 50 bars (5 MPa). The diameter of the nozzle orifice of the vertical extruder was 0.2 mm and the drop printing frequency was 50 drops/sec at the edge of the printed construct and 240 drops/sec for the in-fill. Under these conditions, it was possible to print objects comprising P4HB with good print quality as shown in FIG. 9B.

Example 5: 3D Printing of P4HB by Selective Laser Melting

A P4HB object was printed by SLM using the equipment set up shown in FIG. 10 comprising a moving powder bed equipped with a reservoir for P4HB polymer granules and a powder sweeper, and a laser source that can direct a laser beam on the powder bed. The position of both the moving powder bed and laser beam were controlled by a computer that had been programmed with 3D CAD data to produce a lattice structure of P4HB. The focal distance, the distance between the lens and surface of the powder, shown in FIG. 10, was 50.8 mm. P4HB with Mw=320 kDa, was cryo-milled using liquid nitrogen, and sieved to produce granules with average sizes of 40 to 120 μm. The granules were placed in the powder reservoir, and a first layer of powder was spread on the moving bed using the powder sweeper. The thickness of the powder layer and subsequent layers was 150 μm. The power of the laser was set to 0.3 Watts, and the speed of the laser beam was set at 20 cm/s. Under these conditions, the energy per unit area used was about 1 J/cm$^2$ and the lattice shown in FIG. 11A was printed.

Comparative Example 5: Attempted 3D Printing of P4HB by Selective Laser Melting

An attempt was made to 3D print P4HB by SLM using the equipment set up shown in FIG. 10 comprising a moving powder bed equipped with a reservoir for P4HB polymer granules and a powder sweeper, and a laser source that can direct a laser beam on the powder bed. The conditions used were identical to those described in Example 5, except the average P4HB particle sizes were larger than 250 μm and the laser energy applied per unit area was 0.5 J/cm$^2$. Printing under these conditions failed. FIG. 11B shows the material that resulted under these conditions.

Example 6: 3D Printing of P4HB by Solution Printing by Coagulation Method

A P4HB object was printed by 3D solution printing using the equipment set up shown in FIG. 12 comprising a syringe with a dispensing needle containing a slurry of P4HB, and a movable coagulation bath containing a 70:30 mixture of water and ethanol. The positions of the needle and the coagulation bath could be controlled by a computer that had been programmed with 3D CAD data necessary to print the 3D object. The computer could move the needle in the X and Y directions, and the coagulation bath in the Z direction (where Z is the direction shown in FIG. 12) but keeping the needle tip in the coagulation solvent of the coagulation bath. The diameter of the needle was 100 μm. The slurry was formed by mixing the P4HB polymer at a concentration of 6% w/v with acetone, and was kept at a temperature of 45° C. in the syringe. The 3D P4HB object was printed by applying pressure to the polymer slurry (1800 kPa) so that it exited the moving dispensing needle into the coagulation solvent in the coagulation bath in a continuous manner. The slurry was allowed to precipitate one layer at a time as shown in FIG. 12. Layer upon layer of P4HB was printed in the coagulation bath to form the 3D object at a speed of 15 mm/sec.

Example 7: 3D Printing of P4HB Using a Binding Ink and Granules of P4HB Polymer

A P4HB object was printed using the equipment shown in FIG. 13 comprising a reservoir that can deliver droplets of a binding ink onto a moving powder bed with a reservoir for the P4HB polymer and a powder sweeper. The position of the ejected droplets of binding ink and the position of the moving bed were controlled by a computer loaded with 3D CAD data for the object. The binding inks for fusing the P4HB polymer were acetone, chloroform, dioxane, and tetrahydrofuran. The object was printed by: (i) forming a first layer of P4HB powder granules across the surface of the moving powder bed, and adjusting the thickness of the layer using the powder sweeper to 160 μm, (ii) depositing droplets of binding ink onto the surface of the layer of granules of P4HB powder (Mw=320 kDa) causing the granules to fuse together, (iii) lowering the level of the powder bed (in the Z direction shown in FIG. 13), spreading a new layer of P4HB powder on the moving bed, adjusting the thickness of the powder layer with the powder sweeper, and depositing droplets of binding ink onto the new layer of granules of P4HB powder causing fusion of the granules, and (iv) repeating step (iii) until the object was formed.

The invention claimed is:

1. A method for fabricating a three-dimensional object made from a composition of poly-4-hydroxybutyrate or copolymer or blend thereof, wherein the method comprises:
providing an apparatus for fused pellet deposition, the apparatus comprising (a) a heated pressurized reservoir for polymer pellets fitted at one end with a gas line, (b) a nozzle located at the opposite end of the reservoir to the gas line inlet, (c) a movable stage located underneath the nozzle, and (d) a computer programmed with 3D CAD data for the object that can control the position of the nozzle and stage;
placing pellets of poly-4-hydroxybutyrate or copolymer or blend thereof in the reservoir;
heating the pellets in the reservoir to a temperature of 85 to 180° C.;
pressurizing the reservoir to a pressure of 650 to 2,000 kPa; and
ejecting molten polymer through the nozzle to form the printed object on the stage, wherein the diameter of the nozzle is 0.1 to 1.0 mm.

2. The method of claim 1, further comprising drying the pellets prior to heating the pellets.

3. The method of claim 1, wherein pressurizing the reservoir comprises pressurizing the reservoir with the gas line.

4. The method of claim 1, wherein the gas line comprises at least one of nitrogen or air.

5. The method of claim 1, wherein the apparatus further comprises:
heating jacket surrounding the reservoir; and
a cap fitting arranged on one end of the reservoir.

6. The method of claim 1, wherein the object is printed continuously without interruption of the printing process.

7. The method of claim 1, wherein the average diameter of the pellets are from 0.05 mm to 3 mm.

8. The method of claim 1, wherein the diameter of the nozzle is 0.15 to 0.4 mm.

9. The method of claim 1, wherein the water content of the composition is from 1 ppm to 1,000 ppm.

10. The method of claim 1, wherein cells are incorporated into the object during or after printing.

11. The method of claim 1, wherein the ejecting step includes printing the object with print lines, wherein the dimensions of the print lines are within 10% of the expected dimensions of the print lines.

12. The method of claim 1, wherein the poly-4-hydroxybutyrate or copolymer or blend thereof further comprises one or more of the following: poly(lactide); poly(glycolide); poly(lactide-co-glycolide); poly(lactic acid); poly(glycolic acid); poly(lactic acid-co-glycolic acid); polycaprolactone; poly(orthoester); polyanhydride; poly(phosphazene); polyhydroxyalkanoate; synthetically or biologically prepared polyester, polyester with one or more of the following monomeric units: glycolic, lactic, trimethylene carbonate, p-dioxanone, or ε-caprolactone); poly(lactide-co-caprolactone); polycarbonate; tyrosine polycarbonate; polyamide; polypeptide; polyesteramide; poly(dioxanone); poly(alkylene alkylate); polyether, polyethylene glycol, polyvinyl pyrrolidone; polyurethane; polyetherester; polyacetal; polycyanoacrylate; poly(oxyethylene)/poly(oxypropylene) copolymer; polyacetal, polyketal; polyphosphate; phosphorous-containing polymer; polyphosphoester; polyalkylene oxalate; polyalkylene succinate; poly(maleic acid); chitin; chitosan; modified chitosan; polysaccharides; alginate; silk; glycerol; gelatin; hyaluronic acid and derivatives thereof; collagen; polyvinyl alcohol; and hydrogels.

13. The method of claim 1, wherein the step of heating the pellets in the reservoir comprises heating the pellets to a temperature of 120 to 150° C.

14. A medical implant formed by the method of claim 1.

15. The implant of claim 14, wherein the bioactive agent is selected from the group comprising: small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, peptides, proteins, glycoproteins, anesthetics, hormones, antibodies, growth factors, fibronectin, laminin, vitronectin, integrins, antimicrobials, antibacterial drugs, antiviral agents, antifungal agents, anti-parisitic drugs, steroids, hydroxyapatite, silver particles, vitamins, non steroidal anti-inflammatory drugs, chitosan and derivatives thereof, alginate and derivatives thereof, collagen, sugars, polysaccharides, nucleotides, oligonucleotides, lipoproteins, hyaluronic acid and derivatives thereof, allograft material, xenograft material, ceramics, nucleic acid molecules, antisense molecules, aptamers, siRNA, and nucleic acids.

* * * * *